United States Patent
Densham et al.

(10) Patent No.: US 9,055,226 B2
(45) Date of Patent: *Jun. 9, 2015

(54) SYSTEM AND METHOD FOR CONTROLLING FIXTURES BASED ON TRACKING DATA

(71) Applicant: CAST Group of Companies Inc., Toronto (CA)

(72) Inventors: Gilray Densham, Inglewood (CA); Justin Eichel, Waterloo (CA); Kwok Wai William Law, Scarborough (CA); Weibo Qin, Markham (CA); Florentin Christoph von Frankenberg, York (CA)

(73) Assignee: CAST Group of Companies Inc., Toronto (CA)

( * ) Notice: Subject to any disclaimer, the term of this patent is extended or adjusted under 35 U.S.C. 154(b) by 58 days.

This patent is subject to a terminal disclaimer.

(21) Appl. No.: 13/735,785

(22) Filed: Jan. 7, 2013

(65) Prior Publication Data

US 2013/0128054 A1 May 23, 2013

Related U.S. Application Data

(63) Continuation-in-part of application No. 12/872,956, filed on Aug. 31, 2010.

(51) Int. Cl.
*A61B 5/103* (2006.01)
*H04N 5/232* (2006.01)
(Continued)

(52) U.S. Cl.
CPC .............. *H04N 5/23296* (2013.01); *G02B 7/32* (2013.01); *G03B 21/53* (2013.01); *A43B 1/0054* (2013.01);
(Continued)

(58) Field of Classification Search
CPC .................................................. H04N 5/23296
USPC .......................................................... 348/169
See application file for complete search history.

(56) References Cited

U.S. PATENT DOCUMENTS

| 4,392,187 A | 7/1983 | Bornhorst |
| 4,460,943 A | 7/1984 | Callahan |

(Continued)

FOREIGN PATENT DOCUMENTS

| EP | 1447702 B1 | 2/1997 |
| EP | 0813073 A2 | 6/1997 |
| EP | 2150057 A2 | 2/2010 |

OTHER PUBLICATIONS

Atkinson, D.; Search Report from corresponding PCT Application No. PCT/CA2011/050528; search completed Feb. 11, 2012.

(Continued)

*Primary Examiner* — William C Vaughn, Jr.
*Assistant Examiner* — Luis M Perez
(74) *Attorney, Agent, or Firm* — Blake, Cassels & Graydon LLP.; Wilfred P. So

(57) ABSTRACT

Systems and methods are provided for using tracking data to control the functions of an automated fixture. Examples of automated fixtures include light fixtures and camera fixtures. A method includes obtaining a first position of a tracking unit. The tracking unit includes an inertial measurement unit and a visual indicator configured to be tracked by a camera. A first distance is computed between the automated fixture and the first position and it is used to set a function of the automated fixture to a first setting. A second position of the tracking unit is obtained. A second distance between the automated fixture and the second position is computed, and the second distance is used to set the function of the automated fixture to a second setting.

37 Claims, 27 Drawing Sheets

(51) Int. Cl.
  G02B 7/32    (2006.01)
  G03B 21/53   (2006.01)
  A43B 1/00    (2006.01)
  A61B 5/00    (2006.01)
  A61B 5/11    (2006.01)
  A63B 24/00   (2006.01)
  H04N 5/222   (2006.01)
  H04N 7/18    (2006.01)

(52) U.S. Cl.
  CPC ............... *A61B 5/0002* (2013.01); *A61B 5/112* (2013.01); *A63B 24/0021* (2013.01); *H04N 5/2224* (2013.01); *H04N 7/181* (2013.01)

(56) References Cited

U.S. PATENT DOCUMENTS

| | | | |
|---|---|---|---|
| 4,833,497 A * | 5/1989 | Sugawara | 396/120 |
| 5,150,310 A | 9/1992 | Greenspun et al. | |
| 5,504,477 A | 4/1996 | Whitright et al. | |
| 6,092,914 A | 7/2000 | Esakoff et al. | |
| 6,104,438 A * | 8/2000 | Saito | 348/587 |
| 6,281,930 B1 | 8/2001 | Parker et al. | |
| 6,324,296 B1 | 11/2001 | McSheery et al. | |
| 6,567,116 B1 | 5/2003 | Aman et al. | |
| 6,597,443 B2 | 7/2003 | Boman | |
| 6,710,713 B1 | 3/2004 | Russo | |
| 6,769,771 B2 * | 8/2004 | Trumbull | 352/243 |
| 7,327,383 B2 | 2/2008 | Valleriano et al. | |
| 7,395,181 B2 | 7/2008 | Foxlin | |
| 7,483,049 B2 | 1/2009 | Aman et al. | |
| 7,629,995 B2 | 12/2009 | Salivar et al. | |
| 7,712,365 B1 | 5/2010 | James | |
| 7,720,554 B2 | 5/2010 | DiBernardo et al. | |
| 7,725,279 B2 | 5/2010 | Luinge et al. | |
| 8,019,490 B2 * | 9/2011 | Ferren et al. | 701/3 |
| 8,180,114 B2 | 5/2012 | Nishihara et al. | |
| 8,231,506 B2 | 7/2012 | Molyneux et al. | |
| 8,289,185 B2 | 10/2012 | Alonso | |
| 8,300,302 B2 | 10/2012 | Hewlett et al. | |
| 8,449,141 B1 * | 5/2013 | Hinrichs | 362/235 |
| 8,506,093 B2 * | 8/2013 | Kato | 353/101 |
| 2004/0143176 A1 | 7/2004 | Foxlin | |
| 2007/0021208 A1 | 1/2007 | Mao et al. | |
| 2007/0135243 A1 | 6/2007 | LaRue et al. | |
| 2007/0273766 A1 | 11/2007 | Wilson | |
| 2010/0026809 A1 | 2/2010 | Curry | |
| 2010/0164862 A1 | 7/2010 | Sullivan | |
| 2010/0245588 A1 | 9/2010 | Waehner et al. | |
| 2011/0007158 A1 | 1/2011 | Holtz et al. | |

OTHER PUBLICATIONS http://www.premier-lighting.com/sales/autopilot.html; Wybron AutoPilot 2; Turn Moving Lights into Real-Time Tracking Followspots!; retrieved from the internet Dec. 28, 2012.

http://www.martin.com/productnews/productnews.asp?=8&Words=trackpod; Martin TrackPod wins PLASA Award for Product Excellence; retrieved from the internet Dec. 27, 2012.

http://www.wybron.com/products/tracking_systems/autopilot/; Autopilot II; retrieved from the internet Dec. 27, 2012.

Field, Matthew et al; "Motion capture in robotics review.", Control and Automation, 2009. ICCA 2009. IEEE Internatioanl Conference on, IEEE, Piscataway, NJ, USA, Dec. 9, 2009.

Parnian, N. et al; "Position sensing using integration of a vision system and inertial sensors", Industrial Elecronics, 2008. IECON 2008. 34TH Annual Conference of IEEE, IEEE, Piscataway, NJ, USA, Nov. 10, 2008.

Damp, Stephan; Supplementary European Search Report from corresponding EP patent application serial No. EP11820968; search completed May 28, 2014.

* cited by examiner

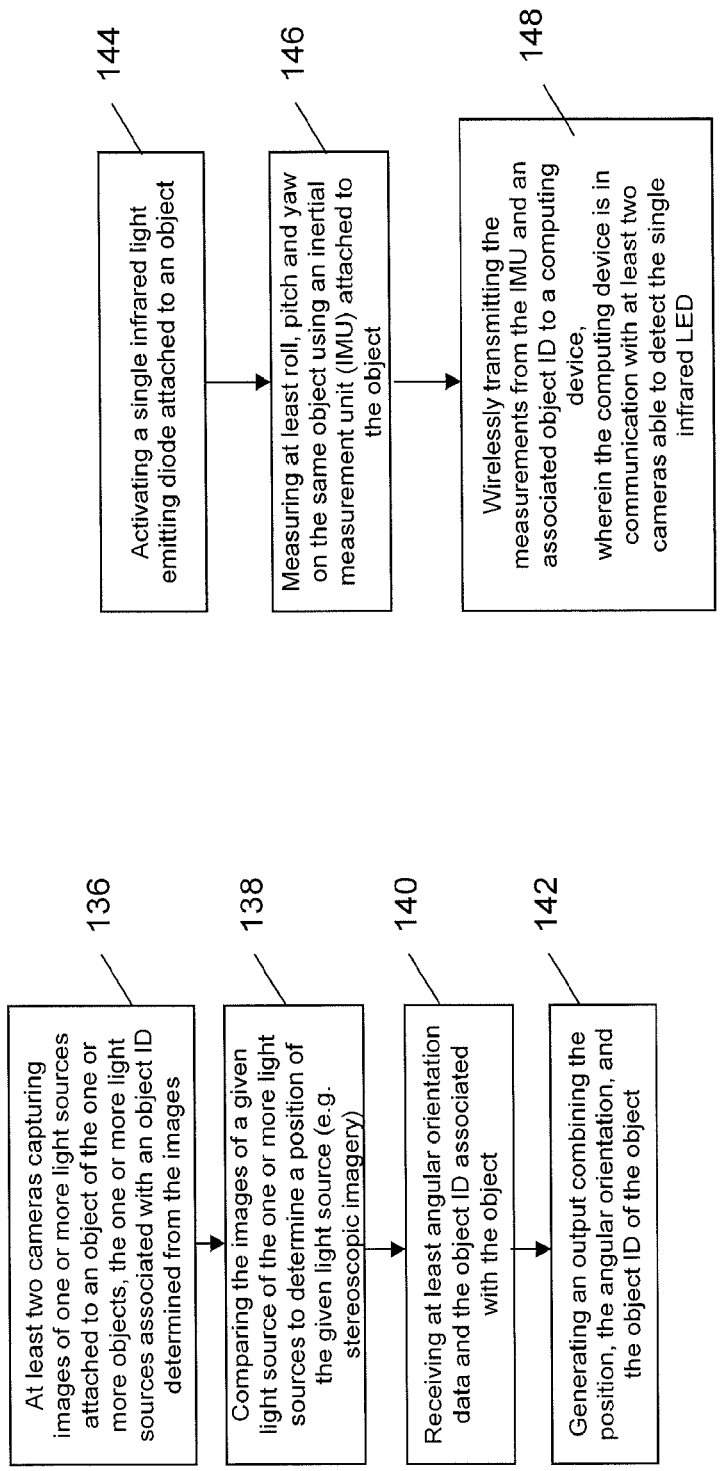

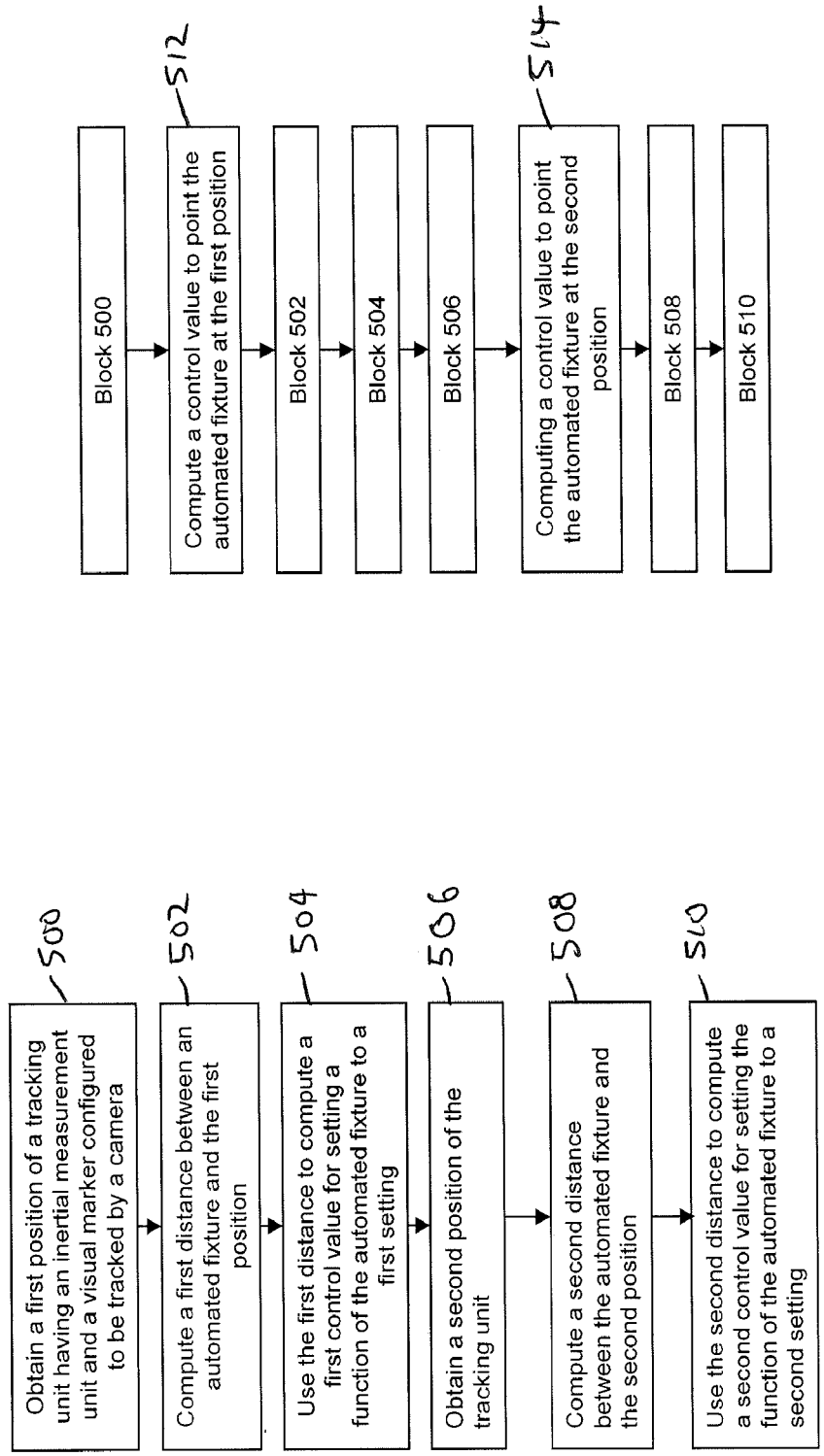

Example: Maintaining constant field of view

Example: Changing a beam diameter to accommodate two or more tracking units where: beam diameter B > beam diameter A Example: Maintaining constant field of view

SYSTEM AND METHOD FOR CONTROLLING FIXTURES BASED ON TRACKING DATA

CROSS-REFERENCE TO RELATED APPLICATIONS

This application is a continuation-in-part of U.S. patent application Ser. No. 12/872,956, filed Aug. 31, 2010, and titled "System and Method for Tracking", the entire contents of which are incorporated herein by reference.

TECHNICAL FIELD

The following relates generally to controlling an automated fixture using tracking data.

DESCRIPTION OF THE RELATED ART

Tracking an object can be difficult, especially when the object's movements are unpredictable and erratic. For example, accurately tracking the movement of a person or an animal can be difficult. Known tracking systems attempt to capture such movement using visual imaging systems. However, processing the images can be resource intensive and slow down the tracking response rate. Other known tracking systems that are able to quickly track movements tend to be inaccurate. The inaccuracy usually becomes more problematic as the sensors are positioned further away from the object being tracked, and if there are other disturbances interrupting the tracking signals.

BRIEF DESCRIPTION OF THE DRAWINGS

Embodiments will now be described by way of example only with reference to the appended drawings wherein:

FIG. 7 is a flow diagram illustrating example computer executable instructions for tracking an object from the perspective of the tracking engine.

FIG. 8 is a flow diagram illustrating example computer executable instructions for providing tracking data from the perspective of the tracking unit.

FIG. 21 is a flow diagram illustrating example computer executable instructions for controlling a function of an automated fixture.

FIG. 22 is a flow diagram illustrating further example computer executable instructions for controlling a function of an automated fixture.

FIG. 20(b) shows the camera fixture capturing a plane with the same given field of view, with the plane including a second position of the tracking.

DETAILED DESCRIPTION

Figure 1:
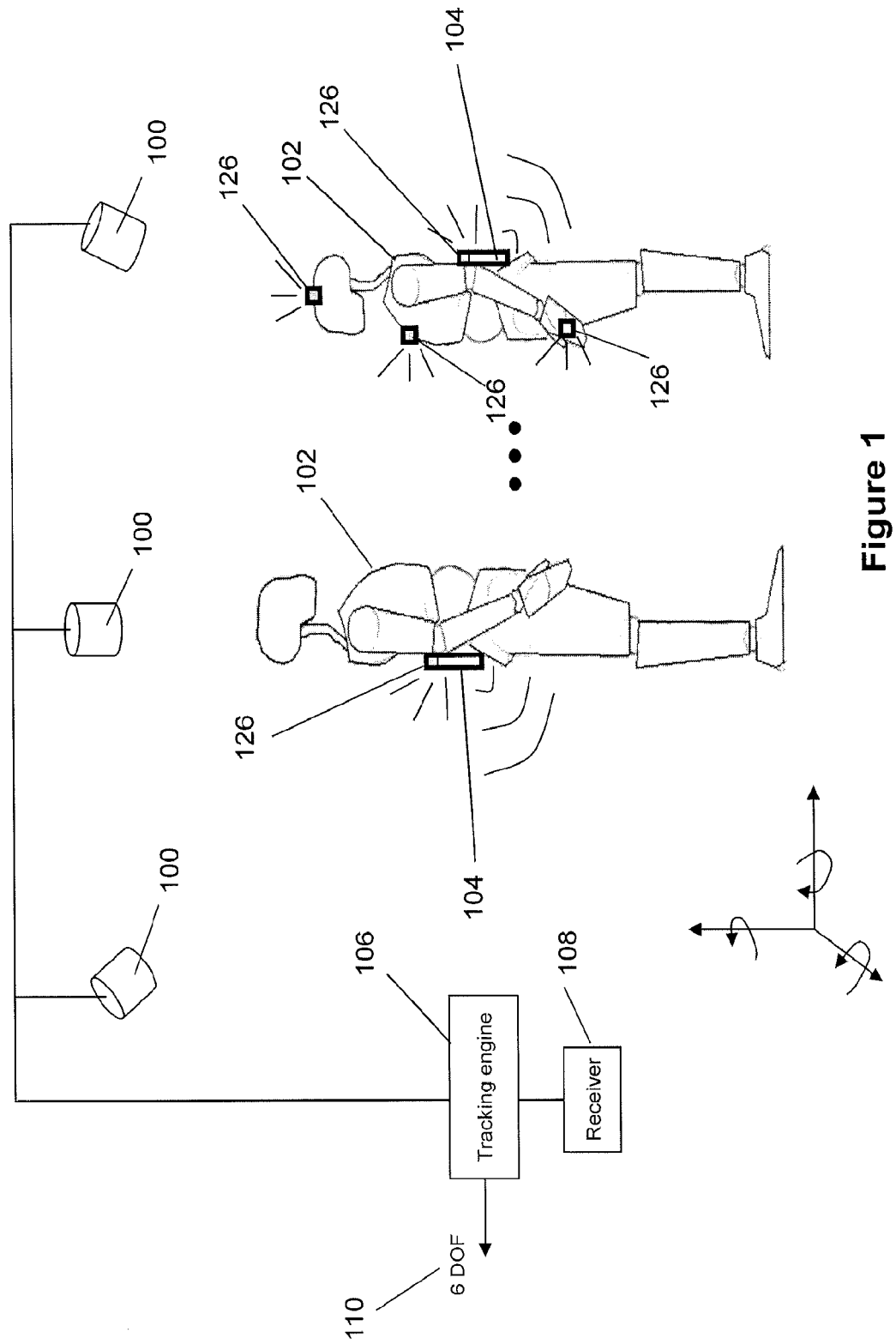
FIG. 1 a schematic diagram of a tracking engine tracking the position and angular orientation of one or more objects.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

In the field of tracking systems, it is known to use image tracking as one approach. However, it has been recognized that image tracking can become increasingly ineffective without proper lighting conditions. Further, image tracking is limited in its tracking range. Objects further away from a camera cannot be easily tracked. Moreover, the proposed systems and methods desire to track multiple objects simultaneously in real time. However, known image tracking systems have difficulty achieving such tracking performance for various reasons (e.g. complexity of object recognition and objects blocked from sight).

Other known tracking systems relate to inertial measurements, such as measuring changes in angular orientation and position over time. However, such systems are considered to be less accurate than image tracking techniques that are capable of providing absolute positioning.

It is also known that robotic lights can be controlled to automatically follow a certain object based on tracking the object's position. However, accurately tracking the object in real-time or near real-time is difficult, and this may lead to a robotic light inaccurately attempting to shine a light on a moving object. Moreover, it is recognized that many control systems for robotic lights are limited to controlling the direction at which a robotic light is pointing.

In general, systems and methods are provided for tracking an object (e.g. position and angular orientation). The system includes a computing device in communication with at least two cameras, each of the cameras able to capture images of one or more light sources attached to an object of the one or more objects. The one or more light sources are associated with an object ID able to be determined from the images. The system also includes a receiver in communication with the computing device, whereby the receiver is able to receive at least angular orientation data and the object ID associated with the object. The computing device determines the object's position by comparing the images of the one or more light sources and generates an output comprising the position, the angular orientation data, and the object ID of the object.

In another aspect, each of the cameras are able to capture images of a single light source attached to the object. In another aspect, each of the one or more light sources comprise an infrared light emitting diode and the cameras are sensitive to infrared light. In another aspect, the receiver is also able to receive inertial acceleration data associated with the object. In another aspect, the angular orientation data comprises roll, pitch, and yaw and the position comprises X, Y, and Z coordinates. In another aspect, the angular orientation data is measured by one or more gyroscopes attached to the object. In another aspect, the inertial acceleration data is measured by one or more accelerometers attached to the object. In another aspect, a given light source of the one or more light sources is associated with the object ID able to be determined from the images by: the receiver also receiving inertial acceleration data associated with the object; the computing device determining an acceleration and a position of the given light source by comparing a series of images of the given light source captured by the cameras; and, upon determining that the acceleration determined from the series of images is approximately equal to the received inertial acceleration data, the computing device associating the received object ID with the given light source's position. In another aspect, a given light source of the one or more light sources is associated with the object ID able to be determined from the images by: the computing device detecting from a series of images a strobe pattern associated with the given light source; and, upon determining that the detected strobe pattern matches a known strobe pattern having a known object ID, the computing device associating the known object ID with the given light source's position. In another aspect, upon associating the given light source's position with the object ID, the computing device determines if a subsequent position of the given light source in subsequent images is within an expected vicinity of the given light source's position, and if so, associating the object ID with the subsequent position. In another aspect, the computing device only compares the images of the one or more light sources that have a strobe pattern. In another aspect, the system further comprises a transmitter, wherein the computing device is able to send a beacon mode selection via the transmitter to control when the one or more lights are displayed and when the angular orientation data is received. In another aspect, the computing device comprises a state machine that uses a Kalman filter or an extended Kalman filter to generate the output comprising the position and the angular orientation of the object. In another aspect, upon the computing device detecting that only one of the cameras is able to detect the light source, or none of the cameras are able to detect the light source: the computing device identifying a last known position of the object as determined from the images; and, the computing device determining a new position of the object by combining the inertial acceleration data with the last known position.

A tracking apparatus that is able to be attached to an object is also provided. The tracking apparatus includes one or more infrared light sources; an inertial measurement unit able to measure at least roll, pitch and yaw; a wireless radio for transmitting at least measurements obtained from the inertial measurement unit and an associated object ID; and, wherein the one or more infrared light sources are able to be detected by at least two cameras and the measurements are able to be transmitted to a computing device that is in communication with the cameras.

In another aspect, the one or more infrared light sources is a single infrared LED. In another aspect, the inertial measurement unit is able to measure acceleration along the X, Y and Z axes. In another aspect, the tracking apparatus further comprises a battery for powering the tracking apparatus. In another aspect, the tracking apparatus further comprises a processor, wherein the processor controls the single infrared light emitting diode with a strobe pattern. In another aspect, the strobe pattern is associated with the object ID. In another aspect, the tracking apparatus further comprises a memory for storing one or more beacon modes, the one or more beacon modes determining at least one of: which one or more types of measurements obtained from the inertial measurement unit are to be transmitted; a time period that the single infrared LED is active; and a time period that measurements obtained from the inertial measurement unit are transmitted to the computing device. In another aspect, the tracking apparatus further comprises a belt, wherein the belt is able to be wrapped around the object.

Turning to FIG. 1, a schematic diagram of a tracking engine 106 for outputting position and angular orientation data of one or more objects is provided. Objects or people 102 can be tracked by having attached to them a tracking unit 104. Each object has a tracking unit 104 which is able to measure at least angular orientation data and able to activate one or more light sources 126. Two or more cameras 100 are used to track the position of the light sources 126. The camera images of the light sources 126 are sent to the tracking engine 106 for processing to determine the absolute position of the object 102. The measured angular orientation data is transmitted, preferably, although not necessarily, wirelessly, to the tracking engine 106, for example through the receiver 108. Preferably, the tracking unit 104 is wireless to allow the objects 102 to move around freely, unhindered. The tracking engine then combines the position data and angular orientation data to generate a six-degrees-of-freedom output (e.g. X, Y, Z coordinates and roll, pitch, yaw angles).

The light source 126 can be considered a passive reflective marker, a heating element, an LED, a light bulb, etc. The light from the light source 126 may not necessarily be visible to the human eye. An active light source is preferred to allow the cameras to more easily track the light source. It has also been recognized that light sources visible to the human eye can be distracting. Furthermore, visible light sources can also be washed out or overpowered by other light, such as by spot lights, which make the light source 126 difficult to track using the camera images. Therefore, it is preferred, although not required, that the light source 126 be an infrared light source, such an infrared LED, since its light energy is more easily detected amongst the other types of lights being used. Further, infrared sensitive cameras can be used to detect only infrared light, thereby increasing the accuracy of tracking a light source. It can therefore be appreciated that an infrared LED and use of infrared sensitive cameras reduces the effects of various (e.g. bright or low-level) light conditions, and reduces visual distractions to others who may be seeing the tracking unit 104. The active infrared LEDs can also be viewed at very far distances.

As shown in FIG. 1, some objects may have a single light source 126, while other objects may have multiple light sources 126. It can be appreciated that at least one light source 126 is sufficient to provide image tracking data, although multiple light sources 126 can increase the image tracking of an object from various angles. For example, if a person 102 is being tracked by cameras 100, the light sources 126 can be more easily seen by the cameras 100 if the light sources are placed on different parts of the person 102 (e.g. the head, the back, the hands, and the front of the person). In this way, as the person turns or moves around, although one light source 126 is occluded from the cameras, another light source 126 remains visible to the cameras 100.

In another embodiment, a single light source 126 that is associated with an object is preferred in some instances because it is simpler to track from an image processing perspective. By only processing an image of a single light source that corresponds to an object, the response time for tracking the object can be much faster. The benefits are compounded when attempting to track many different objects, and each single light source that is imaged can be used to represent the number of objects. The single light source sufficiently provides the positional data, while allowing the tracking engine 106 to very quickly process the locations of many objects. Moreover, using a single light source 126 in each tracking unit 104 conserves power, and thus the length or period of operation of the tracking unit 104.

It can also be appreciated that two or more cameras are used to provide tracking in three dimensions. Using known optical tracking methods, the cameras' 2D images of the light source 126 are used to triangulate a 3D position (e.g. X, Y, Z coordinate) for the light source 126. Although two cameras are sufficient for determining the position, more than two cameras (e.g. three cameras) can provide more accurate data and can track an object from more angles.

Further, each of the light sources 126 can be pulsed at certain speeds or at certain strobe patterns. The pulsing or strobe pattern can be used to distinguish a visual tracking signal of a tracking unit 104 from other lights sources (e.g. stage lighting, car lights, decorative lights, cell-phone lights, etc.) that are within the vicinity of the tracking unit 104. In this way, the other non-tracking light sources are not mistakenly perceived to be the tracking light sources 126. The light sources 126 can also be pulsed at different speeds or at different strobe patterns relative to other tracking light sources 126, in order to uniquely identify each object. For example, a first light source 126 can pulse at a first strobe pattern, while a second light source 126 can pulse at a second strobe pattern. The first and second light sources 126 can be uniquely identified based on the different strobe patterns. In other words, many different objects can be individually tracked and identified using few cameras.

It can therefore be seen that the combination of the image tracking and inertial tracking accurately provides six degrees of freedom at very high response rates. Further, the objects can be tracked from far distances. Additionally, multiple objects can be tracked by simply attaching a tracking unit 104 onto each object that is to be tracked.

Figure 2:
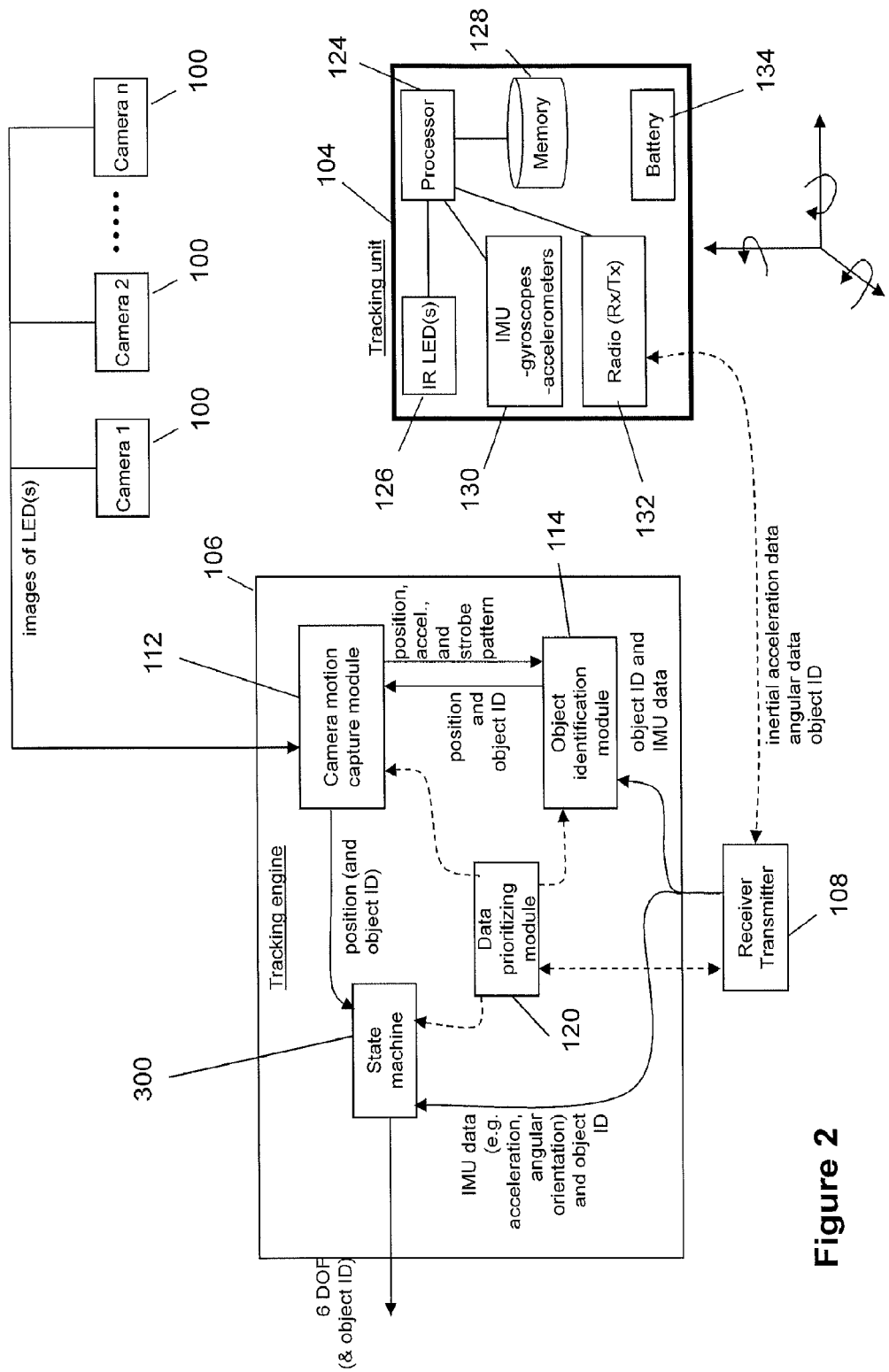
FIG. 2 is a block diagram of an example configuration of a tracking engine and tracking unit.

Turning to FIG. 2, an example configuration of a tracking unit 104 and a tracking engine 106 are shown. The tracking unit 104 includes a processor 124, one or more infrared LEDs 126, an inertial measurement unit (IMU) 130, a radio 132, memory 128 and a battery 134. It is noted that an infrared LED 126 is one of many different types of light sources 126 that can be used herein, and thus, reference numeral 126 is used interchangeably with the infrared LED and with light sources in general. Although a battery 134 is shown, it can be appreciated that the tracking unit 104 can be powered through alternate known means, such as power chords. Further, although a radio 132 is shown, it can be appreciated that other wired or wireless communication devices can be used with the tracking unit 104. It can be appreciated that the packaging or assembly of the tracking unit or tracking apparatus 104 can vary. For example, the LED 126 may be located on one part of the object and the IMU 130 may be located on another part of the object. In another example, the LED 126 could be attached to the object by attaching the LED 126 to the object, and connecting the LED 126 to the processor 124 through wired or wireless communication. The tracking unit or tracking apparatus 104 can be attached to an object using a belt, fastener, adhesive, clip, weld, bolts, etc. In another embodiment, more than one tracking unit 104 can be attached to an object. For example, when tracking different body parts on a person, one tracking unit 104 can be placed on an arm, another tracking unit 104 can be placed on the person's waist, and another tracking unit 104 can be placed on a leg. It can therefore be appreciated that the tracking unit 104 can be attached to an object in various ways.

The battery 134 can be rechargeable and is used to power the components of the tracking unit 104. The IMU 130 may comprise three axis gyroscopes and three axis accelerometers for measuring angular orientation and inertial acceleration, respectively. The angular orientation information and inertial acceleration measured from the IMU 130 is wirelessly transmitted through the radio 132 to the tracking engine 106. As described above, other data communication methods and devices are also applicable. The processor 124 also associates with the IMU data an object identification. The object identification can be stored in memory 128. As discussed earlier, tracking units 104 can be associated with a strobe pattern. Therefore, the memory 128 can store the strobe pattern for the infrared LED 126 and the associated object identification. The processor 124 retrieves the object identification and wirelessly transmits the object identification with the IMU measurements; this data is received by the receiver and transmitter 108 at the tracking engine 106. The processor 124 also retrieves the strobe pattern associated with the object identification and controls the flashing of the infrared LED 126 according to the strobe pattern. The processor 124 also has the ability to send commands, for example, through the radio 132, to activate operations in other control devices. Although not shown, in an embodiment using wireless communication, the antennae of the receiver and transmitter 108 can be physically attached to the cameras 100 in order to create a wireless mesh allowing the tracking engine 106 to more easily communicate with the one or more tracking units 104. In other words, each camera 100 can attached an antenna of the receiver and transmitter 108. The wireless communication can, for example, use the Zigby protocol.

Figures 3, 4:
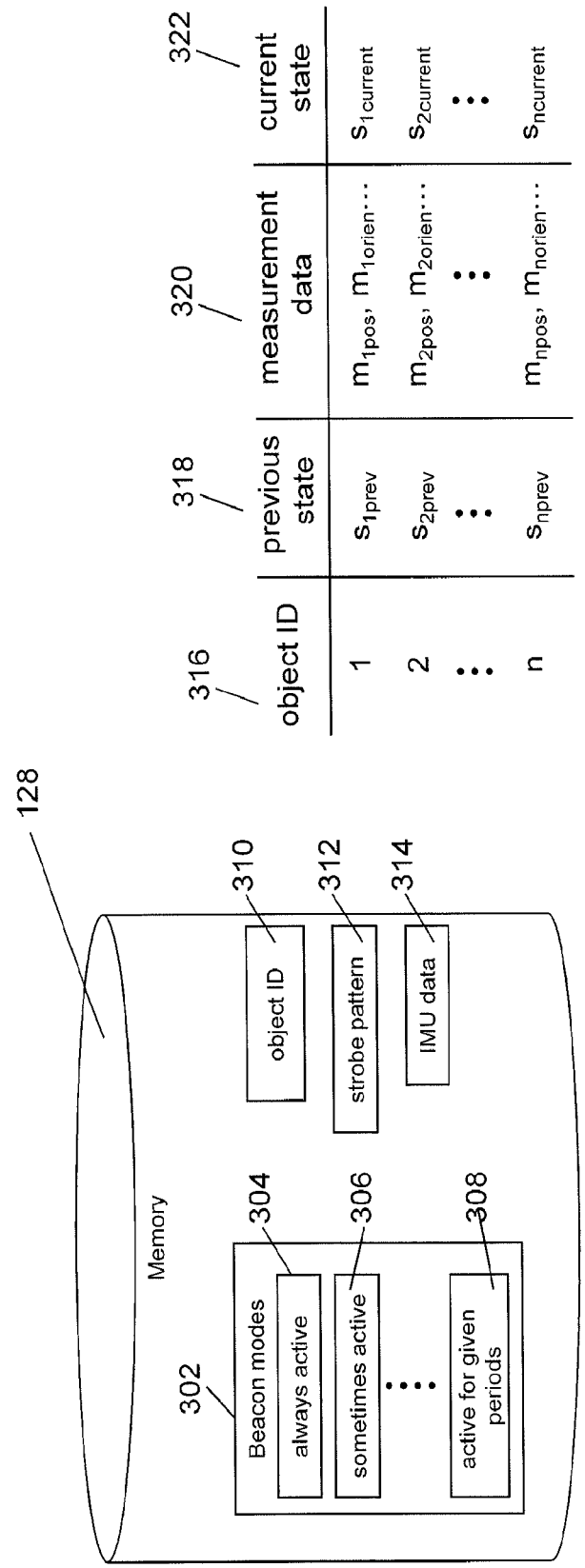
FIG. 3 is a block diagram of example data components in the tracking unit's memory.
FIG. 4 is a schematic diagram of example data components in the tracking engine's state machine.

Turning briefly to FIG. 3, an example of data components are shown in the tracking unit's memory 128. The memory 128 includes an object ID 310, a strobe pattern 312, and IMU data 314. Any data, such as IMU data 314, that is transmitted from the tracking unity 104 to the tracking engine 106 is accompanied by the object ID 310. In this way, the tracking engine 106 can correlate the tracking unit data with an object ID 310. As described above, the strobe pattern 312 is also associated with the object ID 310. In some cases the strobe pattern 310 is unique from other strobe patterns to uniquely identify the object ID 310. The memory 128 also includes beacon modes 302, which determine the manner in which the tracking unit 104 gathers and transmits data to the tracking engine 106. Example beacon modes include "always active" 302, "sometimes active" 306 and "active for given periods" 308. In mode 304, the tracking unit 104 always activates the one or more light sources 126 and always transmits angular orientation data, acceleration data, etc. In mode 306, the tracking unit 104 sometimes activates the one or more light sources 126, and sometimes transmits the IMU data. In mode 308, the one or more light sources 126 are active for only certain or predetermined periods of time and the IMU data is transmitted at the same times. Other beacon modes 302 (not shown) may include activating the one or more light sources 126 but not the IMU 130, or vice versa. It can be appreciated that the beacon modes 302 may be selected using controls, such as buttons or switches, (not shown) on the tracking unit. In addition, or in the alternative, the beacon modes 302 may be selected by the tracking engine 106. The tracking engine 106 can send commands to the tracking unit 104 to select different beacon modes 302. It can be appreciated that selecting different beacon modes 128 can help manage the processing of data by the tracking engine 106. For example, objects that are considered important can have attached tracking units 104 that are in an "always active" beacon mode 304. Objects considered less important can have attached tracking units 104 that are in a "sometimes active" beacon mode 306. In this way, less data is obtained and processed by the tracking engine 106, thereby reducing the tracking engine's processing load.

Although not shown, the tracking unit 104 can include other devices, such as magnetometers and gravity sensors, to measure other attributes.

Turning back to FIG. 2, the light from the infrared LED 126 is detected by two or more cameras 100. The cameras 100 are preferably able to acquire images at a high rate and are connected to the tracking engine 106 in a way to increase data transfer. For example, the cameras can gather images at 240 frames per second and are connected in a star configuration. The cameras may also be Ethernet gray scale cameras that provide a resolution of 0.8 megapixels. The camera images are sent to the tracking engine 106.

The tracking engine 106 can be a computing device or series of computing devices operating together, herein collectively referred to as a computing device. The tracking engine 106 includes: a camera motion capture module 112 for identifying the one or more light sources and associated data (e.g. position, acceleration, heading, strobe patterns, etc.); an object identification module 114 for identifying objects and associated data; a data prioritizing module 120 for prioritizing the processing and transfer of data; and a state machine 300 for collecting different data measurements and calculating the current state (e.g. position and angular orientation) of one or more objects.

The camera motion capture module 112 receives the images from the cameras 100 and determines the three dimensional position of each infrared LED 126. Known imaging and optical tracking techniques can be used. It will be appreciated, however, that the proposed systems and methods described herein are able to track and identify many objects based on the imaging data, and such systems and methods can be combined with imaging techniques.

The camera motion capture module 112 is also able to detect strobe patterns of the LEDs. In one embodiment, the camera motion capture module 112 uses the strobe patterns to differentiate light sources 126 for tracking from other light sources (e.g. car lights, decorative lights, cell phone lights, etc.) that are not used for tracking. In other words, only light sources 126 having a strobe pattern are tracked for their position.

The camera motion capture module 112 can also extract data for identifying objects. In one approach for identifying an object, the camera motion capture module 112 determines the current position of an infrared LED 126 and sends the current position to the object identification module 114. The object identification module 114 compares the current position with previous positions that are associated with known object IDs. If a current position and a previous position are sufficiently close to one another, taking into account the time elapsed between the position measurements, then the current position of the infrared LED 126 is associated with the same object ID corresponding to the previous position. The object identification module 114 then returns the position and object ID to the camera motion module 112. In another approach, the camera motion capture module 112 determines the acceleration and heading of a given infrared LED 126 and this information is sent to the object identification module 114. The object identification module 114 also receives from a tracking unit 104 acceleration data and an associated object ID. The object identification module 114 then compares the acceleration determined from the camera motion capture module 112 with the acceleration sent by the tracking unit 104. If the acceleration and headings are approximately the same, for example within some allowed error value, then the location of the given infrared LED is associated with the same object ID corresponding to the acceleration data from the tracking unit 104. The object identification module 114 then returns the position of the infrared LED 126 and the associated object ID to the camera motion capture module 112. In another approach for identifying objects associated with the infrared LEDs 126, as described above, the camera motion capture module 112 is able to detect strobe patterns. In addition to using strobe patterns to distinguish non-tracking lights from tracking lights, the strobe patterns can also be used to identify one object from another object. For example, the position and strobe pattern of a certain LED is sent to the object identification module 114. The object identification module 114 holds a database (not shown) of object IDs and their corresponding strobe patterns. The module 114 is able to receive object IDs and strobe patterns from the tracking units 104, via the receiver 108. The object identification module 114 receives the position and strobe pattern from the camera motion capture module 112 and identifies the corresponding object ID based on matching the imaged strobe pattern with known strobe patterns in the database. When a match is found, the position and object ID are sent back to the camera motion capture module 112.

The above approaches for tracking and identifying multiple tracking units 104 and objects can be combined in various ways, or used in alternative to one another. It can be appreciated that the object identification module 114 can also directly output the positions of the infrared LEDs 126 to the state machine 300.

As mentioned earlier, the object ID, angular orientation and inertial acceleration data can be sent by a tracking unit 104 and received by the receiver 108. Preferably, the object ID is included with IMU data, whereby the object ID is associated with the IMU data.

The state machine 300 receives the position and associated object ID from the camera motion module 112 or the object identification module 114. The state machine 300 also receives the IMU data (e.g. acceleration, angular orientation, true north heading, etc.) from the receiver 108. The state machine 300 uses these measurements to update the state models. In one example, the state machine 300 uses a particle filter to update the state models. Examples of such particle filters include the Kalman filter and extended Kalman filter, which are known algorithms for estimating a system's varying quantities (e.g. its position and angular orientation state) using control inputs and measurements. In the proposed systems and methods, the measurement data is gathered from the cameras 100 and IMU 130.

An example of data components in the state machine 300 is shown in FIG. 4. Associated with each object ID 316 is a previous state 318, measurement data 320, and a current state 322. The current state 322 is determined by the measurement data 320 and the previous state 318. Upon determining the current state 322, the current state 322 becomes the previous state 318 in order to calculate the next current state 322. In other words, the current state 322 is updated in a recursive manner.

By way of background, noisy sensor data, approximations in the equations that describe how a system changes, and external factors that are not accounted for introduce some uncertainty about the inferred values for a system's state. When using the Kalman filter, the state machine 300 averages a prediction of a system's state with a new measurement using a weighted average. The purpose of the weights is that values with better (i.e., smaller) estimated uncertainty are "trusted" more. The weights are calculated from the covariance, a measure of the estimated uncertainty of the prediction of the system's state. The result of the weighted average is a new state estimate that lies in between the predicted and measured state, and has a better estimated uncertainty than either alone. This process is repeated every step, with the new estimate and its covariance informing the prediction used in the following iteration. This means that the Kalman filter works recursively and requires only the last "best guess"—not the entire history—of a system's state to calculate a new state. When performing the actual calculations for the filter, the state estimate and covariances are coded into matrices to handle the multiple dimensions involved in a single set of calculations. This allows for representation of linear relationships between different state variables (such as position, velocity, and acceleration) in any of the transition models or covariances.

Particle filters, such as Kalman filters and extended Kalman filters, are able to update a state (e.g. the position and angular orientation) at any time upon receiving measurements. In other words, the receipt of the position measurements and the angular orientation measurements do not need to be synchronized, and the measurements can be received by the state machine 300 in any order. For example, the state machine 300 can receive position data more often than angular orientation data for a particular object, and the state of that particular object will be updated as the new measurements are received. This allows for the state machine 300 to update the objects' states at the fastest speed possible, even if IMU 130 has a slower data-gathering rate compared to the camera motion capture module 112. The particle filters are also versatile as they are able to update the state of an object using different types of data. For example, although the camera motion capture module 112 may not be able to provide position data at times because the light sources 126 are occluded or blocked from the cameras' view, the state machine 300 can receive acceleration data from the tracking unit 104 through the receiver 108. Based on the last known position or state of the object and the acceleration information, the state machine 300 can calculate the new position. In this way, various types of data can be used to generate an updated state (e.g. position and angular orientation).

It will be appreciated that other types of particle filtering algorithms can be used. More generally, algorithms used for updating an object's state (e.g. position and angular orientation) using measurements are applicable to the principles described herein.

Turning back to FIG. 2, the output of information from the tracking engine 106 can be very fast, for example at 50 Hz or more. The data response rate can, for example, be maintained by prioritizing the data. For example, the data prioritizing module 120 can prioritize the gathering of positional data over the angular orientation data, so that the positional data is accurate all the time, while the angular orientation data may be updated although with some delay. Additionally, to conserve computing resources, when computing the position when light sources 126 are occluded, the processing of camera images can be delayed. In particular, when using the inertial positioning data, the camera images are not relied upon to determine the position of the LED and, thus, there is no need to process the camera images as quickly.

As described earlier, the data processing speed can further be increased by managing the data flow tracking units 104. The data prioritizing module 120 in the tracking engine 106 can send commands to the tracking units 104 to select different beacon modes 302. By commanding certain of the tracking units 104 to transmit data less frequently (e.g. "sometimes active" mode 306), there will be less data to process. This allows the tracking engine's computing resources to be used to more quickly process the data (e.g. camera images of light sources 126, IMU data, etc.) of those tracking units 104 that output data all time (e.g. "always active" mode 304).

It can be appreciated that the tracking engine 104 outputs both position (e.g. X, Y, Z coordinates) and angular orientation (e.g. roll, pitch, yaw) information associated with an object, or an object ID where there are many objects being simultaneously tracked. Such information is valuable in tracking objects and can be used by other systems. For example, in the security industry or the live entertainment industry, it is desirable to track the position and orientation of hundreds of people simultaneously. The tracking systems and methods described herein can be used to accomplish such tracking. The tracking information outputted by the tracking engine 104 may also be visualized on other computing systems. An example of such a computing system is a real-time tracking module, available under the name BlackBox™ by CAST Group of Companies Inc. Details of a real-time tracking module are provided in U.S. application Ser. No. 12/421, 343, having Publication No. 2010/0073363 to Gilray Densham et al., the contents of which are herein incorporated by reference in its entirety.

Figure 5:
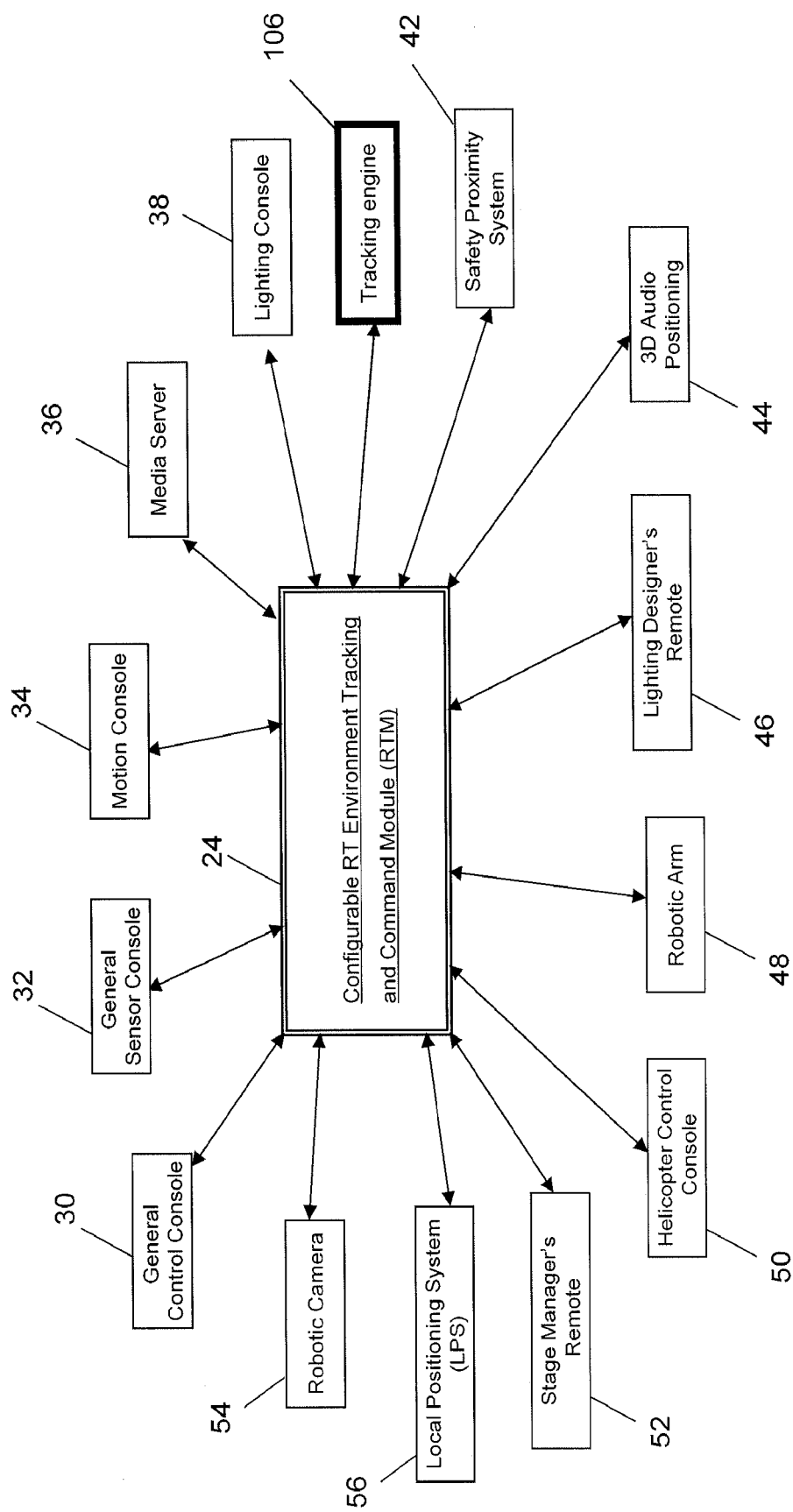
FIG. 5 is a block diagram one configuration of a configurable real-time environment tracking and command module (RTM) connected to various devices, including a tracking engine, for tracking or controlling physical objects.

Turning to FIG. 5, an example configuration of a real-time tracking module (RTM) 24 is shown, whereby the RTM 24 coordinates multiple clients for tracking, visualizing and controlling objects in a three dimensional environment. The various clients connected to the RTM 24 are able to communicate via the RTM 24, either directly or indirectly. Thus, the RTM 24 facilitates the coordination of the clients and enables the clients to interoperate, even when provided by different vendors. In this example, the clients include the tracking engine 106, which provides tracking data of one or more objects in six degrees of freedom. Other clients include a general control console 30, general sensor console 32, motion console 34, media server 36, lighting console 38, safety proximity system 42, 3D audio position system 44, lighting designer's remote 46, robotic arm 48, helicopter control console 50, stage manager's remote 52, and robotic camera 54. The stage manager's remote 52, for example, sends commands to the RTM 24 to control the virtual objects in the virtual environment 4, thereby controlling the media server 36, lighting console 38 and helicopter control console 50. There may also be a local positioning system (LPS) 56 to track a helicopter 23*a*. It can be appreciated that a LPS 56 refers to any device or combination of devices that can determine the location of an object within a localized environment. Examples of devices used in an LPS 56 include RADAR, SONAR, RFID tracking and cameras. The tracking engine 106 is an example of an LPS 56. Such devices are able to measure or sense various characteristics of the physical environment. It can be appreciated that the number and type of clients connected to the RTM 24 as shown in FIG. 5 is non exhaustive. Further, the RTM 24 is configurable to interact with various numbers and types of clients by providing a common, recognizable interface that the client trusts and will enable to interoperate with other clients that it may not otherwise trust.

The interfacing between a client and the RTM 24 is based on predetermined software protocols that facilitate the exchange of computer executable instructions. In other words, a client sends and receives data and computer executable instructions using a file format that is understood by both the client and the RTM 24. Examples of such a file format or protocol include dynamic link libraries (DLL), resource DLLs and OCX libraries. Thus, a client having a file format which is recognized by the RTM 24 may interface with the RTM 24. Once the software interlacing has been established, clients can interact with the RTM 24 in a plug and play manner, whereby the RTM 24 can discover a newly connected client, or hardware component, with little or no device configuration or with little additional user intervention. Thus, the exchange of data between the client and RTM 24 begins automatically after plugging the client into the RTM 24 through the common interface. It can be appreciated that many types of clients are configurable to output and receive a common file format and thus, many types of clients may advantageously interact with the RTM 24. This flexibility in interfacing reduces the integration time as well as increases the number of the RTM's applications. Also, as noted above, this provides the RTM 24 as a trusted intermediate platform for interoperating multiple client types from multiple vendors.

In an example embodiment, a tracking unit 104 can be placed on a helicopter in order to provide feedback on the helicopter's positional coordinates, as well as roll, pitch and yaw. This information is outputted from the tracking engine 106 to the RTM 24, and then sent to the helicopter control console 50. In another example, the tracking unit 104 can be attached or worn by an actor. The actor's position can be tracked and provided to the RTM 24, which interacts with the safety proximity system 42. If the safety proximity system 42, based on the positional data from the tracking engine 106, detects that the actor is moving into a dangerous area, then a safety alert can be generated or a safety action can be initiated.

It can therefore be seen that the tracking engine 106 and tracking unit 104 can be used with a RTM 24.

Figure 6:
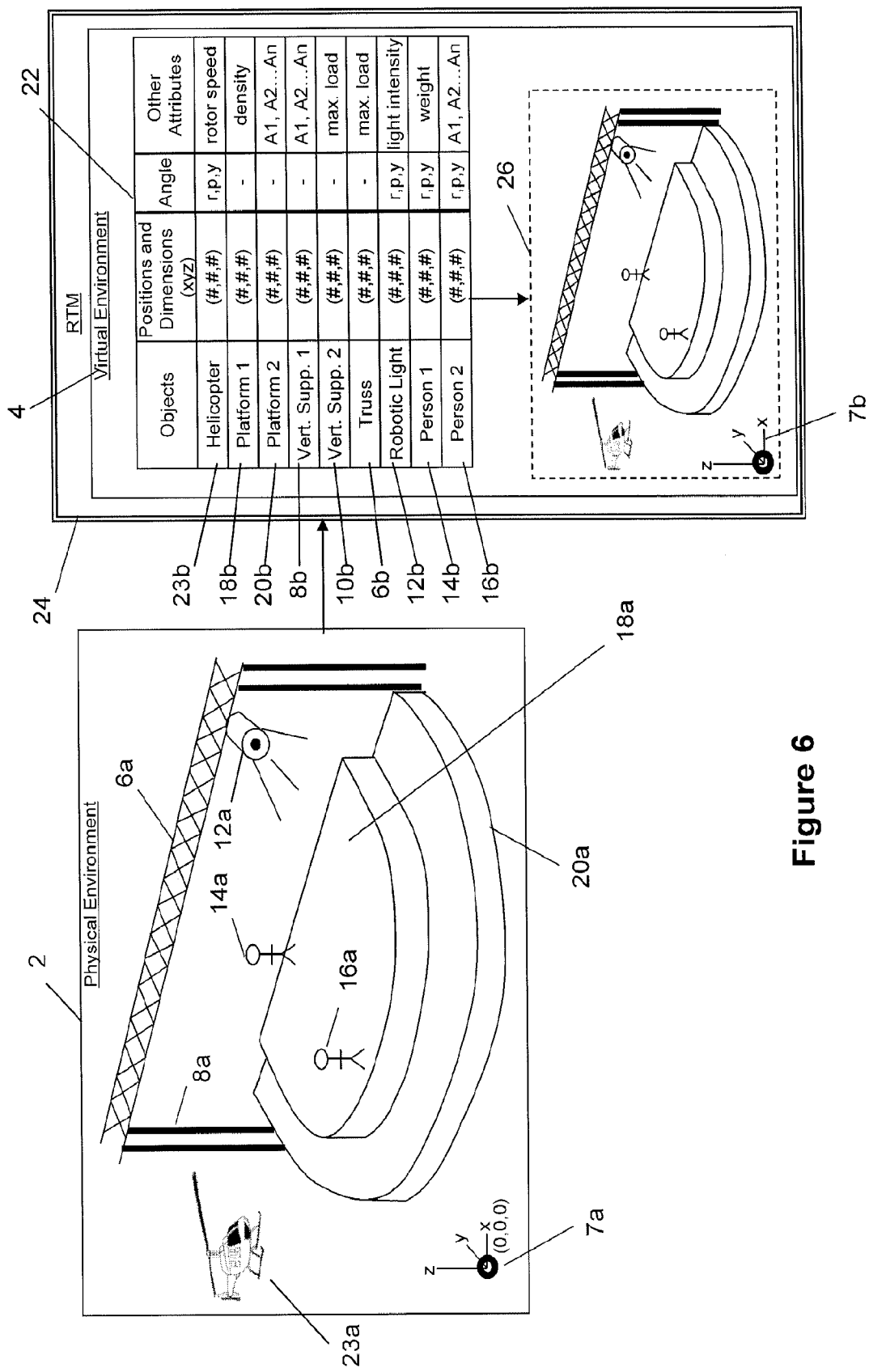
FIG. 6 is a schematic diagram illustrating one example of the generation of a virtual environment from a physical environment using the RTM.

Turning to FIG. 6, further details of the RTM 24 and the use of the tracking engine 106 are provided. A system diagram shows objects in a physical environment 2, in this case a stage, mapping onto a virtual environment 4. It can be appreciated that the virtual environment 4 resides within a computing environment, for example, having various processors, memory, interfaces, computer readable media, etc. Moreover, the virtual environment 4 can also be part of the RTM 24. A memory storage or database 22 of virtual objects and attributes is provided to correspond with the physical objects in the physical environment 2. For clarity, references to physical objects include the suffix 'a' and references to virtual objects include the suffix 'b'. The physical environment 2 in FIG. 3 comprises a first platform 18*a* supported below by a second platform 20*a*. An overhead truss 6*a* extends across the platforms 18*a*, 20*a* and is supported at its ends by two vertical supports 8*a*, 10*a*. A robotic light 12*a* is supported on the truss 6*a* for illuminating the first platform 18*a*, whereupon a first person 14*a* and a second person 16*a* are positioned. A wirelessly controlled helicopter drone 23*a* is flying above the platforms 18*a*, 20*a*. Although not shown, the helicopter drone 23*a*, the first person 14*a*, and the second person 16*a* may each be equipped with their own tracking unit 104. A three-dimensional origin or physical reference point 7*a* is positioned in front of the platforms 18*a*, 20*a*, whereby the positions of the physical objects are measured relative to the physical reference point 7*a*.

Each of these physical objects in the physical environment 2 are mapped onto the virtual environment 22, such that the virtual environment database 22 organizes the corresponding virtual objects and any corresponding attributes. The physical reference point 7*a* is mapped into the virtual environment 22, thus forming a virtual origin or reference point 7*b*. The positions and angular orientations of the virtual objects are mapped relative to the virtual reference point 7*b*. In this example, the virtual objects comprise a virtual helicopter 23*b*, a first virtual platform 18*b*, a second virtual platform 20*b*, a first vertical support 8*b*, a second vertical support 10*b*, a virtual truss 6*b*, a virtual robotic light 12*b*, a first virtual person 14*b*, and a second virtual person 16*b*. Physical attributes corresponding to each physical objects are also represented as virtual attributes corresponding to each virtual object, wherein attributes typically include the position, angular orientation, and dimensions of the objects as well as any data related to movement of the objects (e.g. speed, rotational speed, acceleration, etc.). In one embodiment, the position may be represented in Cartesian coordinates, such as the X, Y and Z coordinates. Other attributes that may also be used to characterize a virtual object include the rotor speed for the helicopter 23*a*, the maximum loads on the truss 6*a*, the angular orientations (e.g. roll, pitch, yaw) and the weight of a person 14*b*. The position and angular orientation of the helicopter 23*a* and the persons 14*a*, 16*a*, are tracked by their respective tracking units 104 and the tracking engine 106. This information is reflected or updated in the virtual environment 4.

It can be appreciated that accurately depicting the virtual environment 4 to correspond to the physical environment 2 can provide a better understanding of the physical environment, thereby assisting the coordination of the clients within the physical environment. The process of depicting attributes of a physical object onto a corresponding virtual object can be considered a physical-to-virtual mapping. Accurately depicting the virtual environment 4 may comprise generating virtual objects based on data automatically provided by clients connected to the RTM 24. Alternatively, some of the virtual objects and their corresponding attributes may be manually entered into the virtual environment database 22. For example, an operator or technician of the RTM 24 may gather the dimensions of a truss and determine its center of mass and volumetric center. The operator may then create a virtual object with the same dimensions, center of mass and volumetric center that corresponds to the truss. The physical location of the truss, with respect to the physical reference point 7*a*, is also used to characterize the location of the virtual object. Thus, the virtual object corresponds very closely to the truss in the physical environment.

Other methods of generating a virtual environment 4 that accurately represent a physical environment include the use of three-dimensional computer drawings, floor plans and photographs. Three-dimensional computer drawings or CAD drawings, using many standard file formats such as .dwg, WYG, Viv, and .dxf file formats, can be uploaded through a conversion system, such as BBX, into the RTM's virtual environment 22. The computer drawings of the virtual objects are scaled to match the dimensions of the physical objects; this mapping process does advantageously reduce the time to generate a virtual environment 4. Additionally, floor plans may be used to generate virtual objects. For example, a floor plan of a house showing the location of the walls may be scanned into digital form in the computer. Then, the walls in the virtual environment are given a height that corresponds to the height of the physical walls. Photographs, including 3D photographs, may also be used to create a virtual environment as they typically illustrate relative dimensions and positions of objects in the physical environment regardless of the scale. An operator may use the photograph to generate a three-dimensional computer drawing or generate a virtual object directly by specifying the dimensions of the object. Photographs may also be used to generate a three-dimensional model using semi or fully automated 3D reconstruction algorithms by measuring the shading from a single photograph, or from a set of point correspondences from multiple photographs.

It can also be appreciated that the location of the physical reference point 7*a* can be positioned in any location. Preferably, the location of the physical reference point 7*a* is selected in a fixed, open area that facilitates consistent and clear measurement of the locations of physical objects relative to the physical reference point 7*a*. As can be seen from FIG. 6, the physical reference point 7*a* is located at the coordinates (0,0,0) in the physical environment. Similarly, the virtual reference point 7*b* is mapped in the same position as the physical reference point 7*a* and is located at the coordinates (0,0,0) in the virtual environment. It can be appreciated that accurate correlation between the reference points 7*a*, 7*b* can be used to calibrate and verify the correspondence between the physical and virtual environments.

Continuing with FIG. 6, a visualization engine 26 uses the information stored in the virtual environment database 22 to generate a graphic, thereby illustrating or visualizing the physical environment 2 to permit interaction with a user. In other words, the visualization engine 26 provides a graphic of the virtual environment 4, which in turn substantially corresponds to the physical environment 2. In the example configuration according to FIG. 6, the visualization engine 26 is part of the virtual environment 4, although not necessarily.

It can therefore be seen that a tracking engine 106 and tracking unit 104 can be used with a RTM 24 to track a person or moving object and display the visualization of the same based on the updated position and angular orientation data in a visualization engine 26.

It will be appreciated that any module or component exemplified herein that executes instructions or operations may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data, except transitory propagating signals per se. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the tracking engine 106 or tracking unit 104 or accessible or connectable thereto. Any application or module herein described may be implemented using computer readable/executable instructions or operations that may be stored or otherwise held by such computer readable media.

Turning to FIG. 7, example computer executable instructions are provided for tracking one or more objects from the perspective of the tracking engine 106. At block 136, at least two cameras capture images of one or more light sources attached to an object of the one or more objects, whereby the one or more light sources are each associated with an object ID able to be determined from the images. At block 138, images of a given light source are compared to determine the three-dimensional position of the light source 126 (e.g. using stereoscopic imagery or triangulation techniques). At block 140, the tracking engine 106 receives at least the angular orientation data and object ID associated with the object. At block 142, an output is generated combining the position, the angular orientation, and the object ID of the object.

FIG. 8 provides example computer executable instructions for tracking an object from the perspective of a tracking unit 104. At block 144, a single infrared LED that is attached to the object is activated. In other instances, multiple other types of light sources can be attached to the same object. At block 146, the tracking unit 104 measures at least roll, pitch and yaw on the same object using an IMU. At block 148, the measurements from the IMU and an associated object ID are wirelessly transmitted to a computing device (e.g. the tracking engine 106), wherein the computing device is in communication with at least two cameras that are able to detect the single infrared LED.

Figure 9:
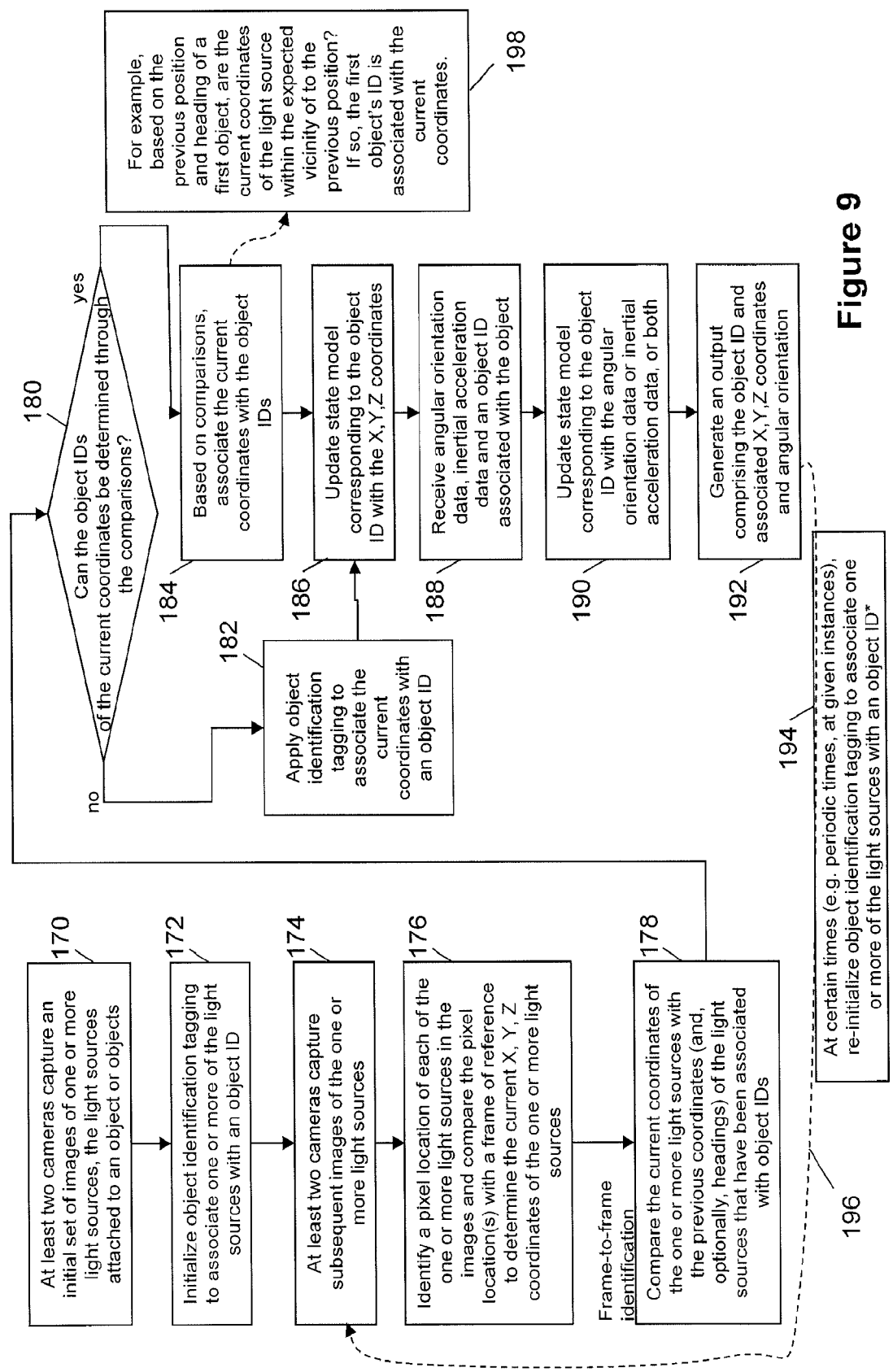
FIG. 9 is a flow diagram illustrating further example computer executable instructions for tracking an object from the perspective of the tracking engine.

Turning to FIG. 9, example computer executable instructions are provided for tracking an object, from the perspective of the tracking engine 106. At block 170, at least two cameras 100 capture an initial set of images of one or more light sources 126, the light sources 126 attached to an object or objects. At block 172, the tracking engine 106 initializes object identification tagging to associate one or more of the light sources with an object ID. Tagging one or more of the light sources with an object ID will be explained below with respect to FIGS. 10 and 11. It can be appreciated that the position of the light sources are also identified when determining the object IDs. Upon associating the light source or light sources with object IDs, the cameras capture subsequent images of the one or more light sources 174. In the subsequent images, a pixel location of each of the one or more light sources is identified. The pixel locations are then compared with a frame of reference to determine the current X,Y,Z coordinates of the one or more light sources.

A frame-to-frame identification approach is then used to determine the object IDs associated with the current coordinates of the light sources. It can be appreciated that methods for tracking objects in video sequences or in consecutive image frames are known. Examples of such frame-to-frame tracking include feature extraction and feature detection. An example of feature extraction or feature detection is "blob detection", which is used to define points of interest that are tracked from frame to frame. At block 178, the current coordinates of the one or more light sources are compared with the previous coordinates (and optionally, headings) of the light sources that have been associated with object IDs. In other words, the positions of known objects are compared with positions of unknown objects. At block 180, it is determined if the objects IDs of the current coordinates can be determined through the comparisons. Such a determination is made by, for example, by determining if the current coordinates (without an object ID) are close enough to the previous coordinates (with an object ID). If not, then the object ID of the current coordinates cannot be determined. Then, at block 192, object identification tagging is applied to associated the current coordinates with an object ID. The approaches for object identification tagging are described with respect to FIGS. 10 and 11.

Continuing with FIG. 9, if at block 180 the object ID can be determined for the current coordinates, at block 184, based on the comparisons, the current coordinates are associated with an object ID. For example, at block 198, based on the previous position and heading of a first object, it is determined if the current coordinates of a light source are within the expected vicinity of the previous position. If so, the first object's ID is associated with the current coordinates.

At block 186, the state machine 300 receives the current coordinates and associated object ID. The state model corresponding to the object ID is then updated with the X, Y, Z coordinates. At block 188, the tracking engine 106 also receives the angular orientation data and object ID associated with the object being tracked. The inertial acceleration data and any other data sent by the tracking unit 104 may also be received. The state model corresponding to the object ID is then updated with the angular orientation data or inertial acceleration data, or both. At block 192, an output is generated comprising the object ID and the associated X, Y, Z coordinates and angular orientation. The process then repeats, as represented by dotted line 196, by returning to block 174. Subsequent images of one or more light sources are captured and used to identify a current location of the object.

At block 194, at certain times (e.g. periodic times, under certain conditions and instances), the object identification tagging of the light sources is re-initialized to associate one or more of the light sources with an object ID. For example, every 5 seconds, instead of using frame-to-frame image tracking, object identification tagging is used.

Figures 10, 11:
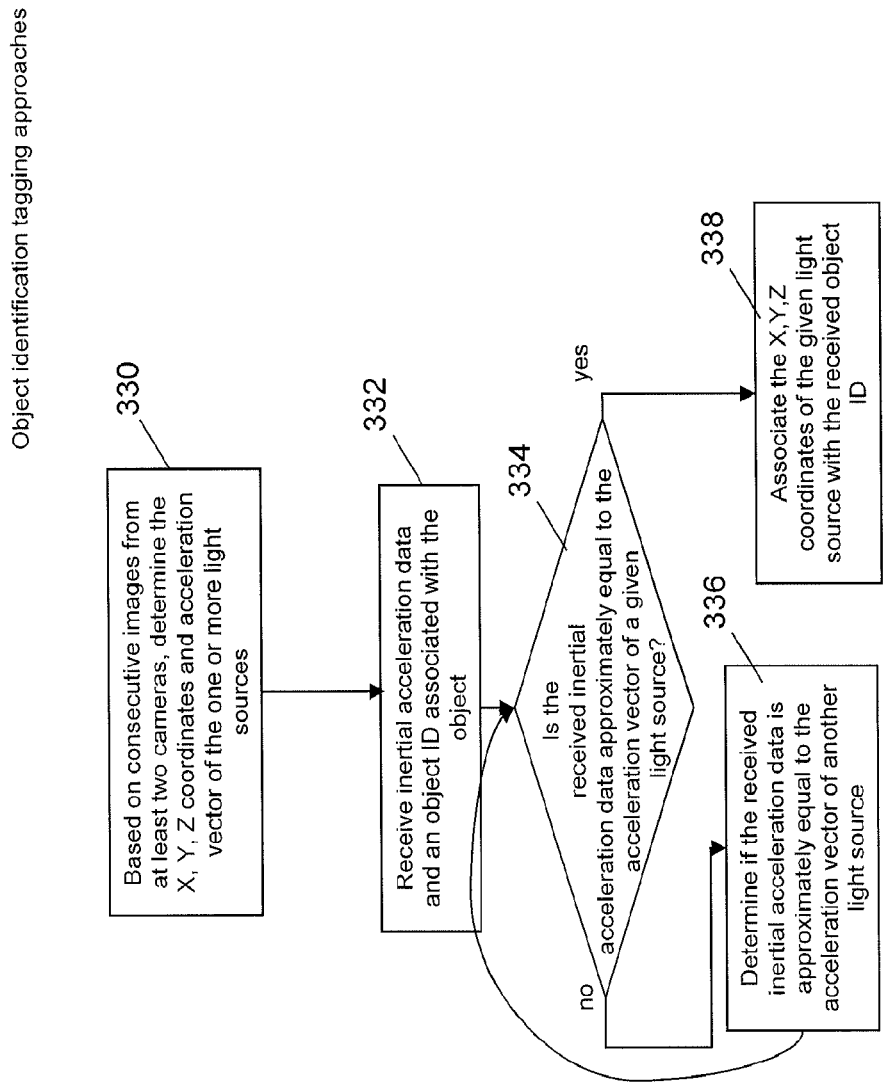
FIG. 10 is a flow diagram illustrating example computer executable instructions for associating an object ID with the position of a light source using acceleration information.
FIG. 11 is a flow diagram illustrating example computer executable instructions for associating an object ID with the position of a light source using strobe pattern information.

Turning to FIGS. 10 and 11, two approaches for object identification tagging are provided. These approaches can be used in combination with the frame-to-frame image tracking, as described above in FIG. 9. FIG. 10 provides computer executable instructions for tracking an object by comparing the visually computed acceleration vector of a light source with the acceleration data (and associated object ID) sent by a tracking unit 104. FIG. 11 provides computer executable instructions for tracking an object by detecting the strobe pattern of a light source and comparing the strobe pattern with a database correlating object IDs and strobe patterns. Either one of the approaches in FIGS. 10 and 11, or both, can be used with the method in FIG. 9.

Turning to FIG. 10, at block 330, based on consecutive images from at least two cameras, the tracking engine 106 determines the X, Y, Z coordinates and acceleration vector of a given light source or light sources associated with an object. At block 332, the tracking engine 106 also receives inertial acceleration data and an object ID, both associated with the same object. At block 334, it is determined whether or not the received inertial acceleration data approximately equals to the acceleration vector of the give light source. For example, if it is detected using the consecutive camera images that a light source is accelerating at 1 m/s$^2$ along the Y axis and the received inertial acceleration data, having a known object ID, measures that the tracking unit 104 is accelerating at 1.01 m/s$^2$ along the Y axis, then the X,Y,Z coordinates of the light source are associated or tagged with the known object ID. However, at block 334, if the acceleration vector from the camera images and the inertial acceleration data from the IMU 130 do not match within a given error tolerance, then it is determined if the received inertial acceleration data is approximately equal to the acceleration vector of another light source. The data-comparison process repeats at block 334 to continue identifying other lights sources.

Turning to FIG. 11, at block 340, based on consecutive images from at least two cameras, the X,Y,Z coordinates are determined and a strobe pattern or strobe patterns are detected, whereby both the coordinates and the one or more strobe patterns are associated with one or more light sources. It can be appreciated that multiple light sources that are part of the same tracking unit 104 can have the same strobe pattern. At block 342, an object ID is identified based on a given strobe pattern (e.g. by comparing the strobe pattern with a database of strobe patterns corresponding to object IDs). When a match between the detected strobe pattern and a strobe pattern in the database is found, then the corresponding object ID in the database is associated with the one or more light sources. At block 344, the X, Y, Z coordinates are associated with the identified object ID, as they both correspond to a same strobe pattern.

Figure 12:
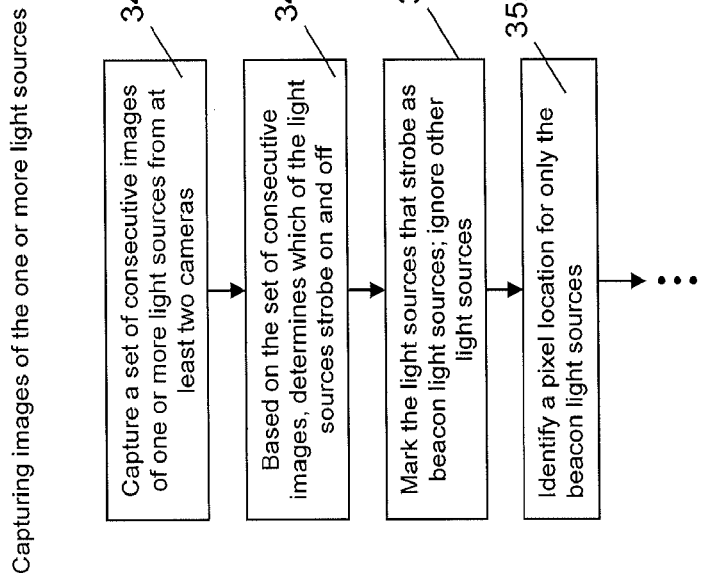
FIG. 12 is a flow diagram illustrating example computer executable instructions for distinguishing and tracking beacon light sources from other non-tracking light sources based on a strobe pattern.

Turning to FIG. 12, example computer executable instructions are provided for capturing images of the one or more light sources (e.g. blocks 170 and 174 shown in FIG. 9). As described above, the light sources 126 used as a tracking beacon can be more easily distinguished from non-tracking light sources when the light sources 126 are pulsing. In particular, at block 346, the tracking engine 106 captures a set or series of images (such as, for example, consecutive images) of one or more light sources from at least two cameras. At block 348, based on the set of consecutive images, the tracking engine 106 determines which of the light sources strobe on and off. At block 350, the tracking engine 106 marks the light sources 126 that strobe as beacon or tracking light sources. The tracking engine 106 ignores the other light sources and does not determine their locations. At block 352, the tracking engine 106 identifies a pixel location for only the marked beacon or tracking light sources. The tracking engine 106 then proceeds to determine the X, Y, Z coordinates or the object ID, or both for the marked beacon or tracking light sources. It will be appreciated that the computer executable instructions described in FIG. 12 can be combined with other systems and methods of tracking described herein.

Figure 13:
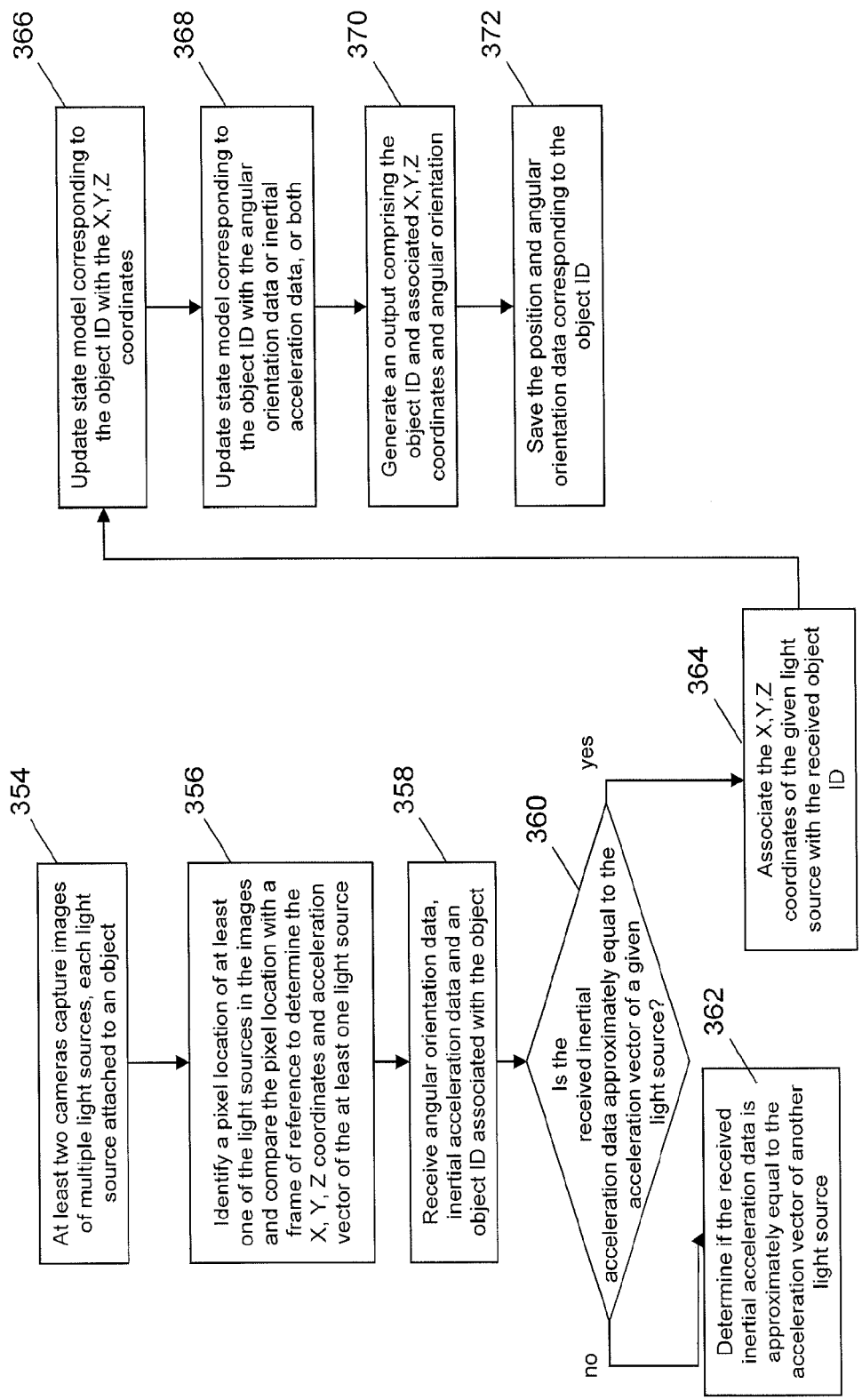
FIG. 13 is a flow diagram illustrating example computer executable instructions for tracking and identifying an object from the perspective of the tracking engine using acceleration information.

In another embodiment, the tracking engine 106 can determine the position coordinates and object ID of a light source 126 by comparing acceleration data and need not use frame-to-frame image tracking as described above. Turning to FIG. 13, example computer executable instructions are provided for tracking and identifying objects by comparing acceleration data determined from camera images and from an IMU 130. At block 354, at least two cameras capture images of one or more light sources, each light source attached to an object. At block 356, the pixel locations of at least one of the light sources in the images is identified, and the pixel locations are compared with a frame of reference to determine the X, Y, Z coordinates and acceleration vector of the at least one light source. At block 358, the angular orientation, inertial acceleration data and object ID associated with the object is received by the tracking engine 106. At block 360, it is determined whether or not the received inertial acceleration data is approximately equal to the acceleration vector of a given light source. If not, then at block 362 it is determined if the received inertial acceleration data is approximately equal to the acceleration vector of another light source, in order to identify a matching object ID. However, if, at block 360, it is determined that the received inertial acceleration data from the IMU 130 does approximately equal the acceleration vector determined from the camera images, then at block 364, the X, Y, Z coordinates of the given light source are associated with the received object ID. At block 366, the state model corresponding to the object ID is updated with the X, Y, Z coordinates. At block 368, the state model corresponding to the object ID is also updated with the angular orientation data or inertial acceleration data, or both. At block 370, the tracking engine 106 generates an output comprising the object ID and the associated X, Y, Z coordinates and angular orientation. At block 372, the position and angular orientation data corresponding to the object ID is saved, for example in the state machine 300.

Figure 14:
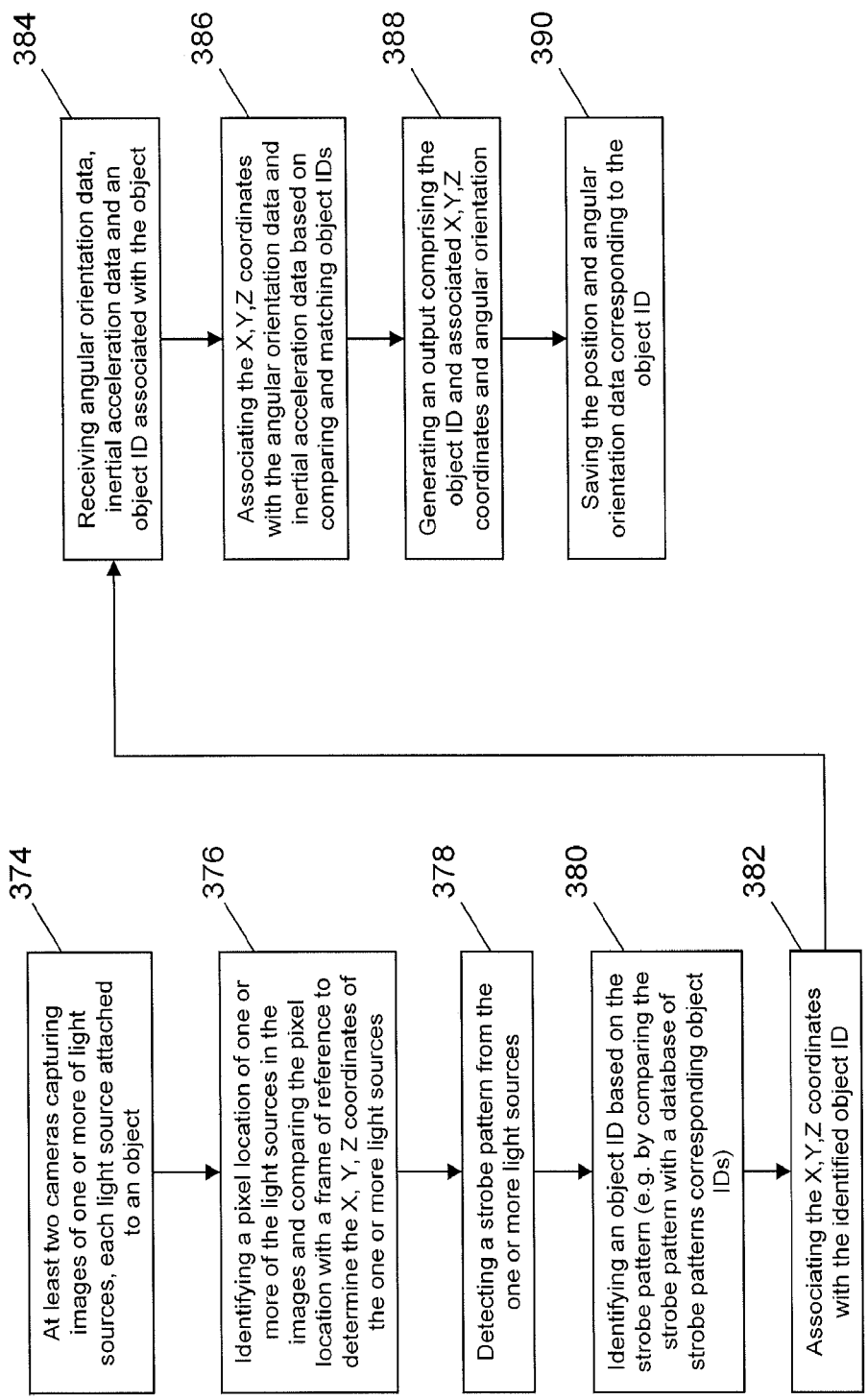
FIG. 14 is a flow diagram illustrating example computer executable instructions for tracking and identifying an object from the perspective of the tracking engine using strobe pattern information.

In another embodiment, the tracking engine 106 is able to track and identify an object or many objects simultaneously using the strobe patterns. The tracking engine 106 in this embodiment does not use frame-to-frame image tracking as described above. Turning to FIG. 14, example computer executable instructions are provided for tracking and identifying an object by comparing strobe patterns with other strobe patterns having associated object IDs. At block 374, at least two cameras capture images of one or more light sources, each light source attached to an object. At block 376, a pixel location of the one or more light sources in the images is identified, and the tracking engine 106 compares the pixel location with a frame of reference to determine the X, Y, Z coordinates of the one or more light sources. At block 378, a strobe pattern is detected from the images of the one or more light sources. At block 380, an object ID is identified based on the detected strobe pattern. For example, the detected strobe pattern is compared with a database of strobe patterns having corresponding object IDs. When a match of strobe patterns is found, the corresponding object ID from the database is also associated with the detected strobe pattern and the coordinates of the strobe light (block 382). At block 384, at least angular orientation data and object ID, and optionally inertial acceleration data, are received by the tracking engine 106. At block 386, the received data (e.g. from the tracking unit 104) is associated with the X, Y, Z coordinates based on comparing and matching the object IDs. The measurements (e.g. coordinates, angular orientation, acceleration, etc.) are used to update the state model corresponding to the object ID. At block 388, an output is generated comprising the object ID and associated X, Y, Z coordinates and angular orientation. At block 390, this data (e.g. current state) is saved in association with the object ID, for example, in the state machine 300.

It can therefore be seen that in the above approaches, hundreds of different objects can be simultaneously tracked based on the using acceleration data, different or unique strobe patterns, frame-to-frame image tracking, and combinations thereof.

Figure 15:
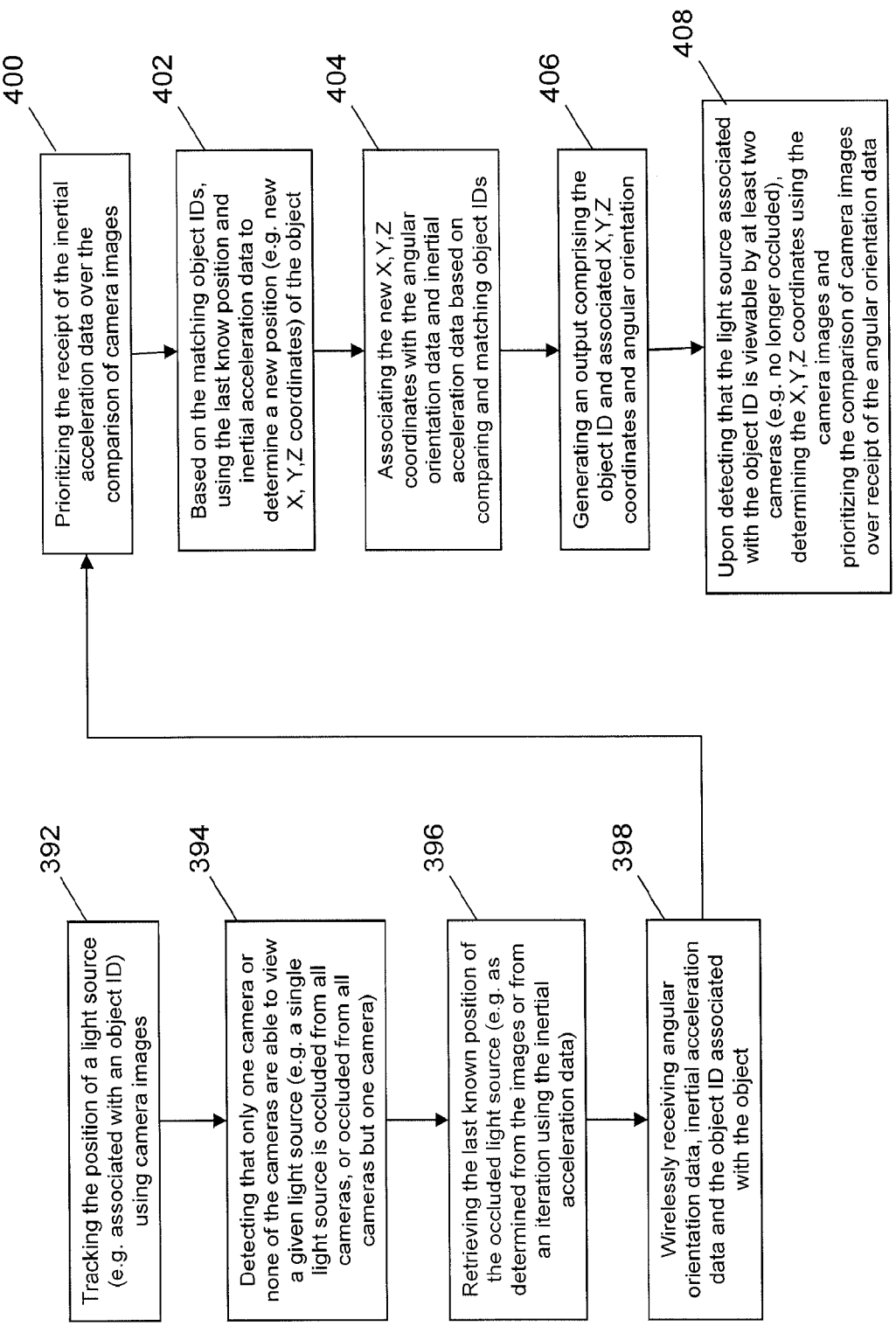
FIG. 15 is a flow diagram illustrating example computer executable instructions for tracking an object when only one camera or none of the cameras are able to view a light source of the tracking unit, from the perspective of the tracking engine.

Turning to FIG. 15, example computer executable instructions are provided for tracking an object, and in particular, switching between tracking approaches under certain conditions. The instructions are provided from the perspective of the tracking engine 106. At block 392, the tracking engine 106 tracks the position of a light source, which can be associated with an object ID, using camera images. At block 394, the tracking engine 106 detects that only one camera can view the single light source, or that none of the cameras are able to view the single light source. In other words, the light source 126 is occluded in a way that an insufficient number of cameras are able to view the light source 126 to obtain a 3D coordinate. At block 396, the last known position of the occluded single light source is retrieved. The last known position can be determined from the images or from an iteration using the inertial acceleration data. At block 398, the tracking engine 106 wirelessly receives the angular orientation data, the inertial acceleration data and the object ID associated with the object. At block 404, the receipt of the inertial acceleration data is prioritized over the comparison of images, thereby allowing critical operations to be processed more quickly. At block 402, based on the matching object IDs, the last known position and the inertial acceleration data are used to determine a new position (e.g. new X, Y, Z coordinates) of the object. At block 404, the new X, Y, Z coordinates are associated with the angular orientation data and the inertial acceleration data based on comparing and matching object IDs. At block 406, an output comprising the object ID, associated X, Y, Z coordinates and angular orientation data is generated. At block 408, upon detecting that the light source associated with the object ID is viewable again by at least two cameras (e.g. no longer occluded), the tracking engine 106 determines the X, Y, Z coordinates using the camera images. The priority of the operations is also updated, whereby the comparison of camera images is given a higher priority over the receipt and processing of angular orientation data.

Figure 16:
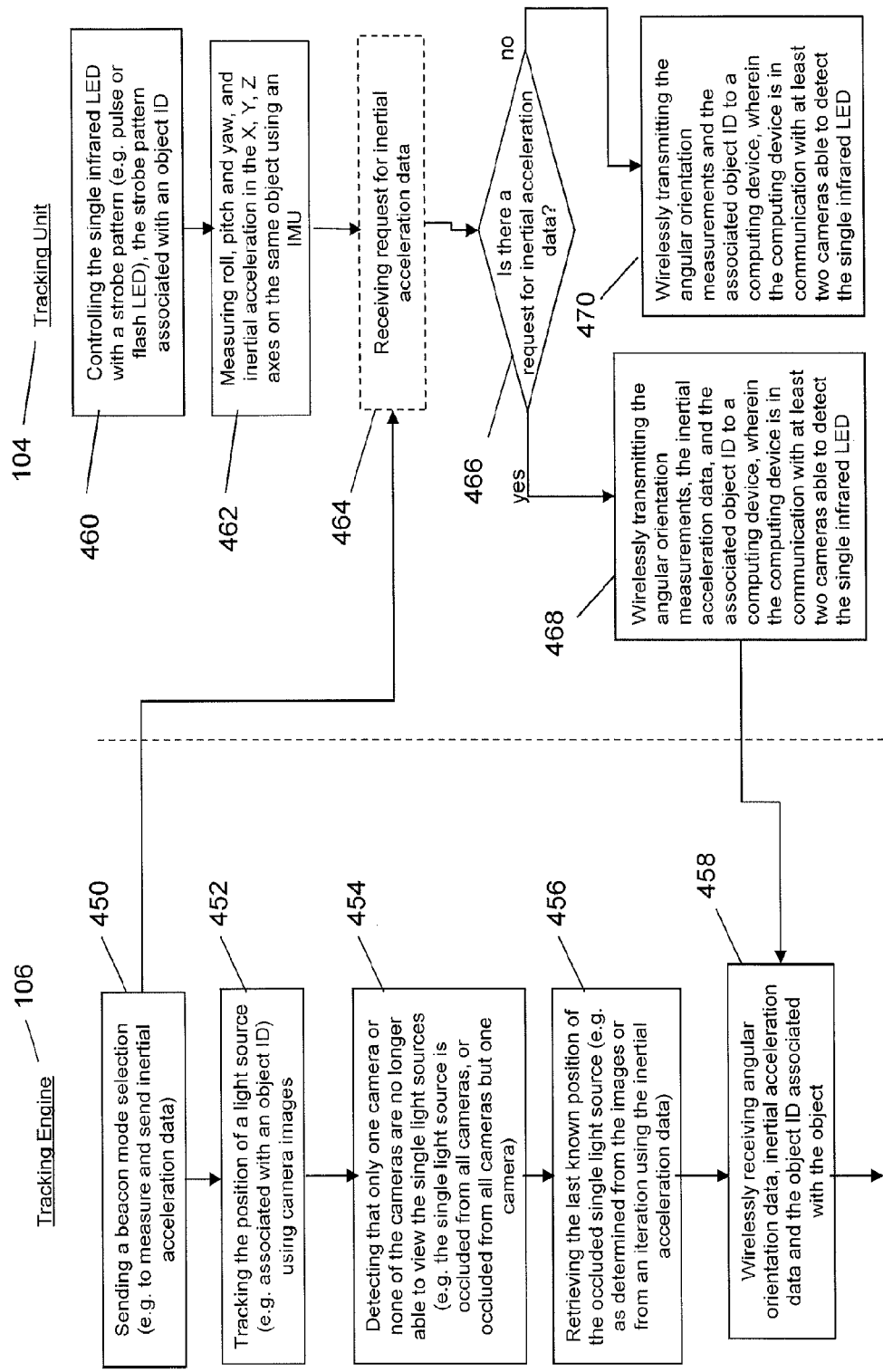
FIG. 16 is a flow diagram illustrating example computer executable instructions for selecting beacon modes for the tracking unit from the perspective of the tracking engine and the tracking unit.

FIG. 16 shows example computer executable instructions between a tracking engine 106 and a tracking unit 104. In some situations, for the benefit of conserving energy and increasing response speed, the inertial acceleration data is only provided by the tracking unit 104 upon the request of the tracking engine 106. As described above, the tracking unit 104 can provide data according to certain beacon modes (e.g. "always active", "sometimes active", "active for given periods of time", etc.). Some of the beacon modes can also include providing certain data, such as just the angular orientation data, or providing both angular orientation data and inertial acceleration data. The beacon modes can be determined by receiving a selection command from the tracking engine 104. At block 450, the tracking engine 106 sends a beacon mode selection to the tracking unit 104, such as to measure and return both angular orientation data and inertial acceleration data. Meanwhile, the tracking unit 104, controls a single infrared LED or multiple light sources with a strobe pattern, whereby the strobe pattern is associated with an object ID. At block 462, the tracking unity 104 measures roll, pitch and yaw and the inertial acceleration in the X, Y, Z axes on the same object using the IMU 130. At block 464, the tracking unit 104 receives from the tracking engine 106 the beacon mode selection for both angular orientation and acceleration data. The tracking unit 104, upon detecting that there is a request for inertial data (block 466), transmits both the angular orientation data, the inertial acceleration data, and the associated object ID to the computing device (e.g. the tracking engine 104). It can be appreciated that the computing device is in communication with at least two cameras able to detect the single infrared LED 126. If the acceleration data is not requested, as per the beacon mode, then only the angular orientation data and the associated object ID are sent to the computing device (e.g. the tracking engine 104) (block 470).

Meanwhile, the tracking engine 106 tracks the position of the light source using camera images (block 452). The tracking engine 106 detects that only one or none of the cameras are no longer able to view the single light sources (block 454). For example, the single light source is occluded from all the cameras, or occluded from all the cameras but one. The last known position of the occluded single light source is retrieved (block 456). Then at block 458, the tracking engine 104 receives the angular orientation data, inertial acceleration data and the object ID associated with the object. The tracking engine 106 can then continue to execute operations set out in blocks 400, 402, 404, 406, and 408, as per FIG. 15.

In one embodiment, the inertial acceleration data is measured at all times. In another embodiment, the inertial acceleration data is measured only in certain beacon modes as selected by the tracking engine 106; this saves energy and increases processing efficiency for both the tracking unit 104 and the tracking engine 106.

Figure 17:
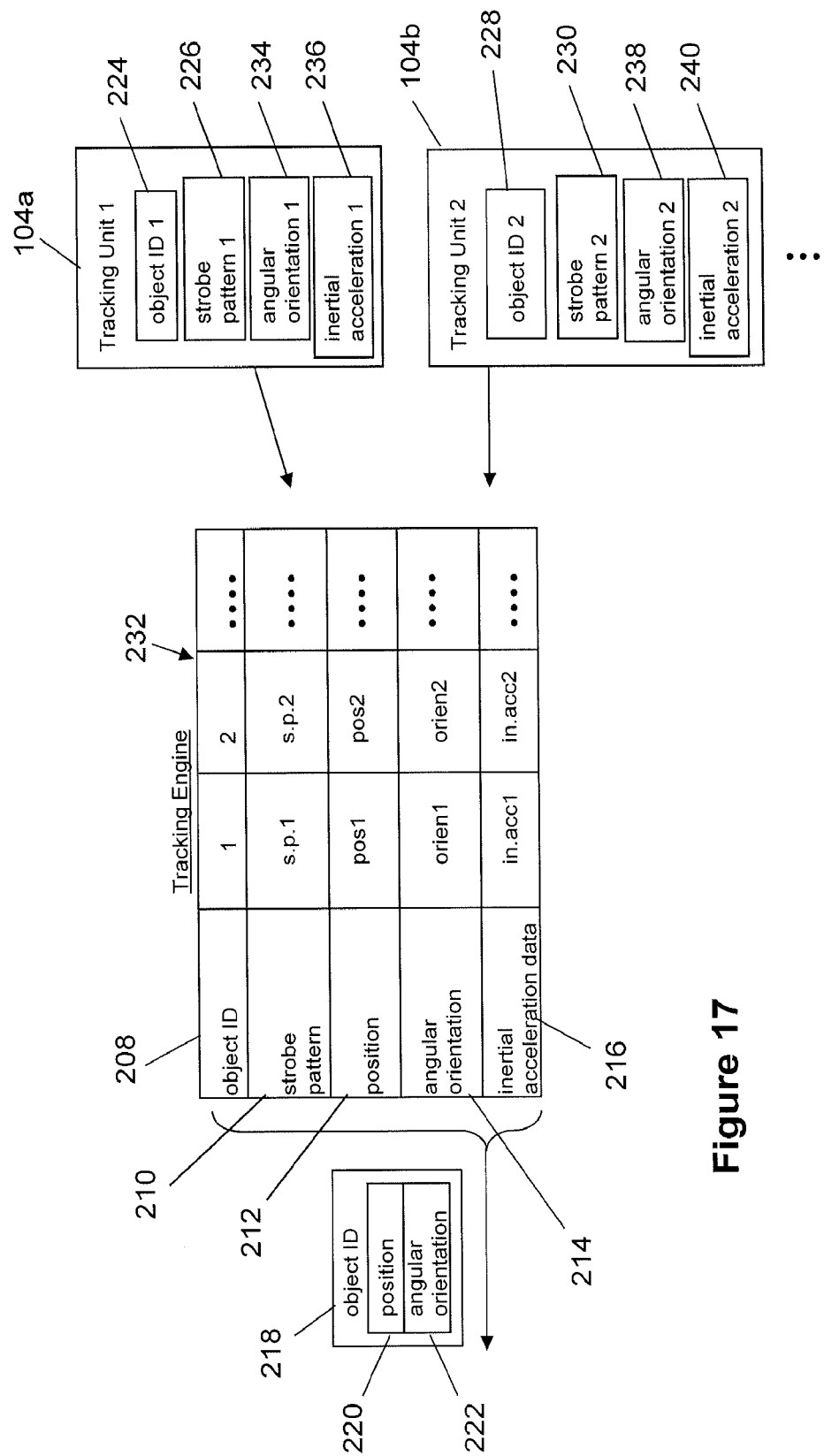
FIG. 17 is a schematic diagram illustrating example data components of the tracking unit and tracking engine.

Turning to FIG. 17, example data components associated with the tracking units 104a and 104b and the tracking engine 106 are shown. In particular, a first tracking unit 104a includes object ID1 (224), strobe pattern 1 (226), angular orientation 1 (234) and inertial acceleration) (236). The IMU measurement data can be, although not necessarily, stored in the tracking unit 104a. Similarly, the second tracking unit 104b is associated with its own object ID 2 (22), strobe pattern 2 (230), angular orientation 2 (238) and inertial orientation 2 (240). The measurement data from both the first tracking unit 104a and the second tracking unit 104b, as well as the object IDs (224 and 228) are sent to the tracking engine 106.

The tracking engine 106 includes a database 232 for storing and associating the object ID 208, the strobe pattern 210, the position data 212, the angular orientation data 214 and the inertial acceleration data 216. This information is organized according to the object IDs. This information, as described above, is also stored in a state model associated with the object ID. The information extracted or outputted from the database 232 includes the object ID 218, as well as the associated position 220 and angular orientation 222.

It can be appreciated that the above systems and methods can be applied to, for example, tracking objects, animals or people, or for any moving or static item whereby its position and its direction of movement are desired to be known. The systems and methods can be used for tracking in lighting, audio, and entertainment marketplaces, military, security, medical applications, scientific research, child care supervision, sports, etc.

In another aspect, the tracking system can be used to vary one or more functions of fixtures. For example, as tracking unit 104 moves a distance, a function's setting of an automated fixture can vary with the change of the tracking unit's distance. Further details are provided below.

In a general example, a method for controlling a function of an automated fixture is provided. It includes: obtaining a first position of a tracking unit, the tracking unit including an inertial measurement unit and a visual indicator configured to be tracked by a camera; computing a first distance between the automated fixture and the first position; using the first distance to set a function of the automated fixture to a first setting; obtaining a second position of the tracking unit; computing a second distance between the automated fixture and the second position; and using the second distance to set the function of the automated fixture to a second setting.

Non-limiting examples of further aspects of the general example are provided below.

In another aspect, after obtaining the first position, the method includes computing a control value to point the automated fixture at the first position. In another aspect, after obtaining the second position, the method includes computing a control value to point the automated fixture at the second position. In another aspect, the automated fixture is a light fixture and the function is a zoom function. In another aspect, the first setting of the zoom function is set to provide a given light beam diameter projected at the first position, and the second setting of the zoom function is set to provide the same light beam diameter projected at the second position. In another aspect, the first setting of the zoom function is set to provide a given light intensity projected at the first position, and the second setting of the zoom function is set to provide the same light intensity projected at the second position.

In another aspect, the automated fixture is a light fixture and the function is an iris function. In another aspect, the first setting of the iris function is set to provide a given light beam diameter projected at the first position, and the second setting of the iris function is set to provide the same light beam diameter projected at the second position.

In another aspect, the automated fixture is a light fixture and the function comprises a zoom function and an iris function. In another aspect, the zoom function and the iris function are set to maintain a constant beam diameter projected at the first position and the second position. In another aspect, the iris function setting is changed when the zoom function is set to a maximum or minimum value, and when a beam diameter associated with the maximum or minimum value of the zoom function needs to be further increased or decreased to provide the constant beam diameter.

In another aspect, the automated fixture is a camera fixture. In another aspect, the function is a zoom function. In another aspect, the first setting of the zoom function is set to provide a given field of view at a first plane include the first position, and the second setting of the zoom function is set to provide the same field of view at a second plane including the second position. In another aspect, the function is a focus function. In another aspect, the first setting of the focus function is set to provide a focus level at a first plane including the first position, and the second setting of the focus function is set to provide the same focus level at a second plane including the second position.

In another aspect, the difference between the first setting and the second setting is proportional to the difference between the first distance and the second distance. In another aspect, the difference between the first setting and the second setting is linearly proportional to the difference between the first distance and the second distance.

Figure 18:
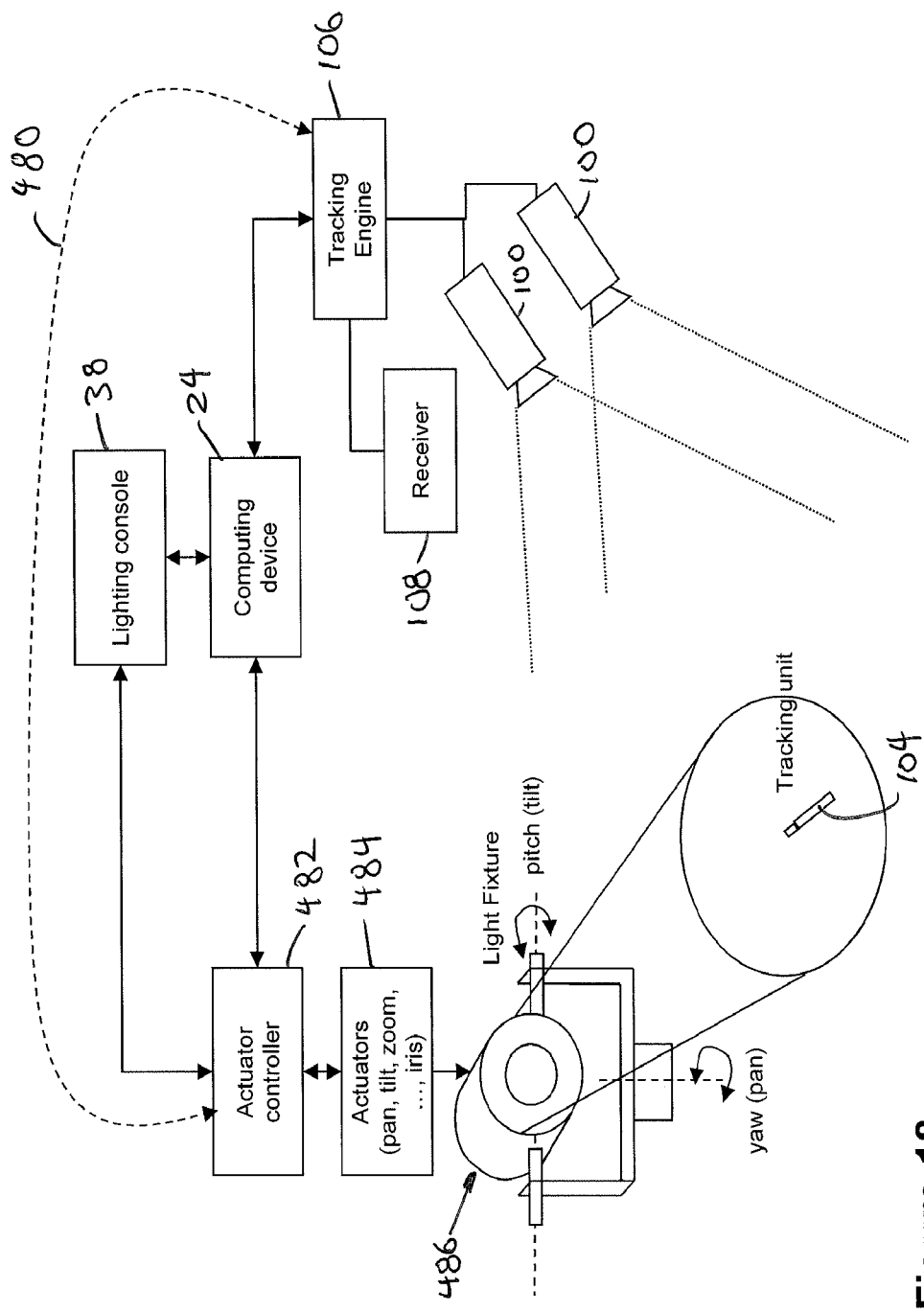
FIG. 18 is a schematic diagram of an example system for controlling a light fixture to automatically shine a light beam on a tracking unit.

Turning to FIG. 18, an example system is provided for an automated fixture to respond to the position of a tracking unit 104. In an example embodiment, a light fixture 486 is controlled using one or more actuators 484. For example, the actuators 484 are used to control the tilt, pan, zoom, dimmer, and iris. Other functions of the light fixture that can be controlled include the color of the light and the focus of the edges of the light beam. A controller 482 can control the actuators 484. The controller 484 can communicate data with a lighting console 38 and a computing device 24. For example, the computing device is the real-time tracking module 24 described above. The computing device 24 can send a control signal to the controller 482 to, in turn, affect the light fixture 486. The lighting console 38 can also exchange data with the computing device 24, and can also be used to receive inputs from the user. For example, a user controls the light fixture 486 using the lighting console 38.

The tracking engine 106 is in communication with the computing device 10. The tracking engine 106 can be used to provide the location of the tracking unit 104 using the cameras 100 and a receiver 108. The computing device 24 uses the position of the tracking unit 104 to compute control signals to point the light fixture at the tracking unit 104. In this way, the light beam tracks or follows the position and movement of the tracking unit 104 in real-time.

In another example embodiment, the computing device 24 is not required. The tracking engine 106 can communicate directly with the light fixture itself, for example with the controller 482 of the light fixture 48 as illustrated by the line 480. Either the tracking engine 106 or the lighting console 38 can compute control signals for the actuator controller 482 to affect the light fixture 486. Various other computing configurations that are applicable the methods described herein can be used.

Figures 19A, 19B:
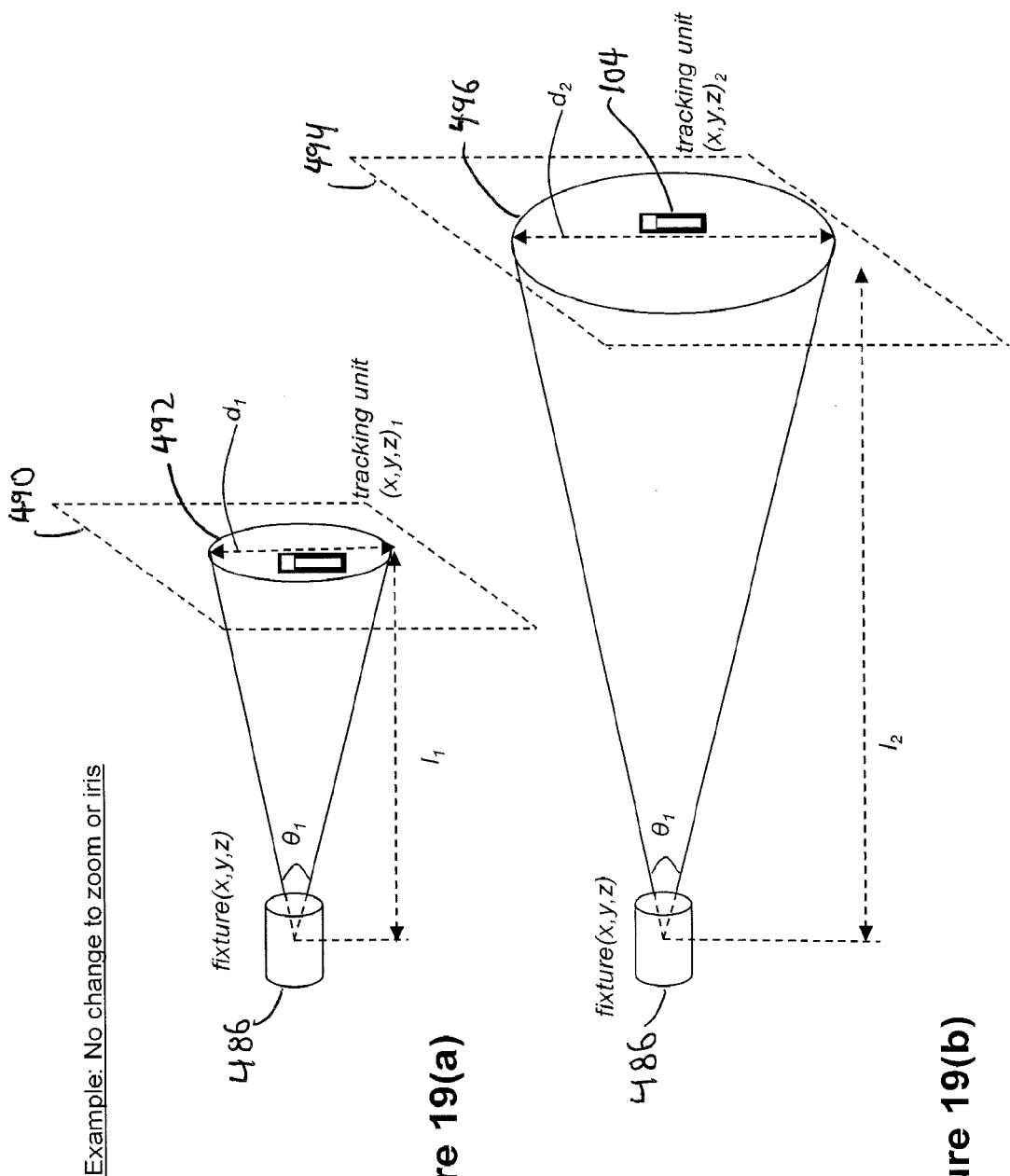
FIG. 19(a) is a schematic diagram of a light beam projected at a tracking unit located a first distance away from a light fixture.
FIG. 19(b) shows the light beam projected at the tracking unit located at a second distance away from the light fixture, with the beam diameter changing with the distances.

Turning to FIGS. 19(a) and 19(b), an example scenario is illustrated of a light fixture 486 shining a light beam at the position of a tracking unit 104. In FIG. 19(a), the distance between the light fixture 486 and the tracking unit's position is $l_1$. In an example embodiment, the light fixture 486 has position co-ordinates x,y,z and the tracking unit has another set of position co-ordinates of x,y,z, and the distance $l_1$ between the light fixture and the tracking unit is computed by $(\Delta x^2 + \Delta y^2 + \Delta z^2)^{1/2}$. On a plane 490 which includes the position of the tracking unit, also located at distance 1, away from the fixture 486, the beam 492 cast onto the plane 490 has a diameter $d_1$. The outputted beam angle is $\theta_1$. The outputted angle of the beam can be controlled using the zoom function or iris function, or both, of the light fixture.

In FIG. 19(b), the outputted beam angle remains at $\theta_1$, but the tracking unit 104 has moved to a different position that is located further away from the fixture 486. The new distance $l_2$ is greater than $l_1$. With such conditions, the beam diameter 496 that is cast on to the different plane 494, which includes the further position of the tracking unit, is larger. In other words, the beam diameter $d_2$ is larger than $d_1$.

Figures 20A, 20B:
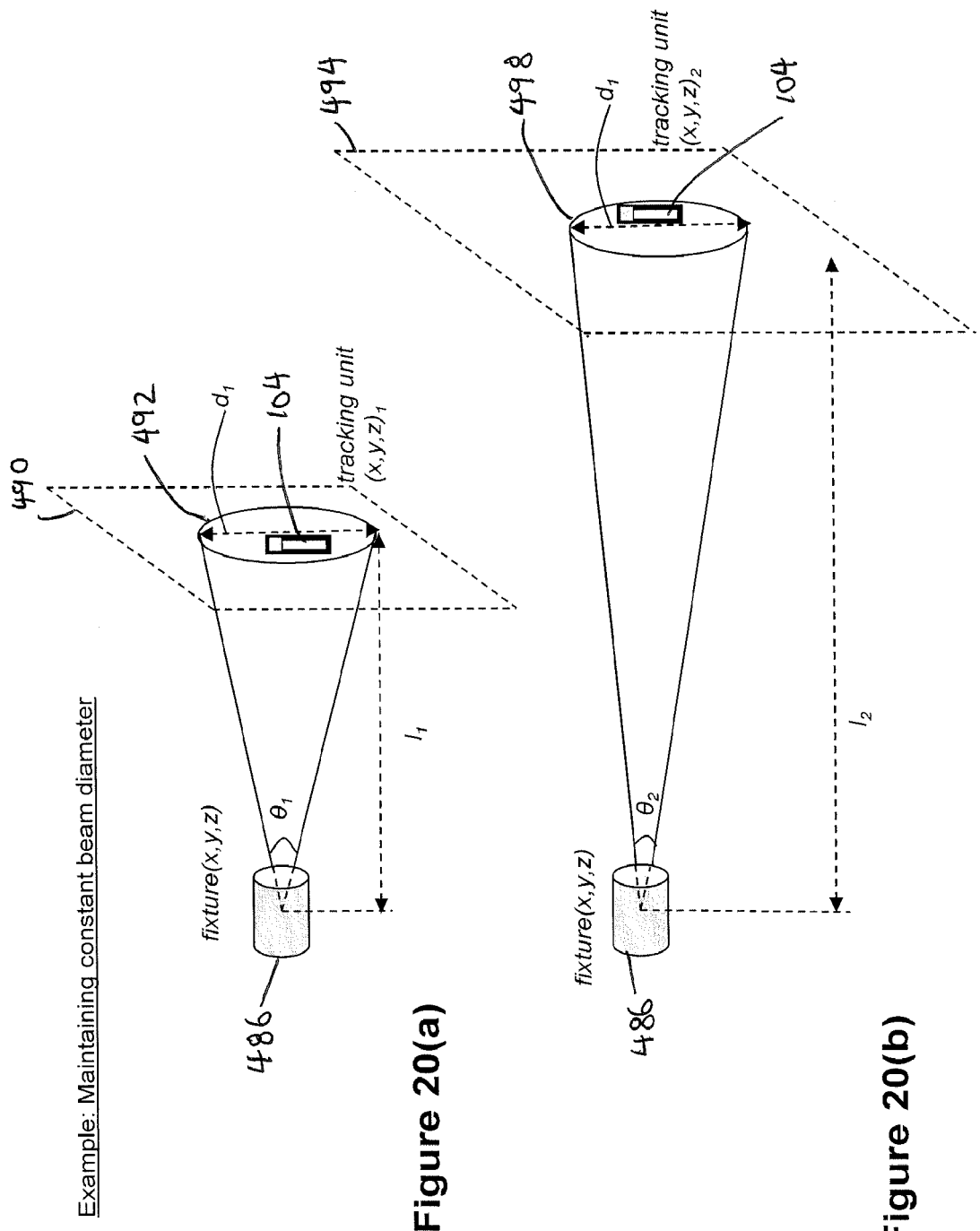
FIG. 20(a) is a schematic diagram of a light beam projected at a tracking unit located a first distance away from a light fixture.
FIG. 20(b) shows the light beam projected at the tracking unit located at a second distance away from the light fixture, with the beam diameter remaining the same with the distances.

Turning to FIGS. 20(a) and 20(b), another example embodiment is shown which illustrates how the zoom function or iris function, or both, are varied according to the change in position of the tracking unit 104 to maintain a constant beam diameter. FIG. 20(a) is the same as FIG. 19(a).

Turning to FIG. 20(b), when the tracking unit 104 has moved to a further position at a distance of $l_2$ away from the fixture 486, the fixture's zoom function or iris function, or both, is varied to maintain the same beam diameter size $d_1$ that is being projected on the plane 494 that includes the further position of the tracking unit. The process of implementing such control is described generally in FIG. 21.

Turning to FIG. 21, an example embodiment of computer executable instructions is provided for controlling a function of an automated fixture. These instructions can be executed by the tracking engine 106, the computing device 24, or a control console for the automated fixture. The device executing such instructions is hereafter generally referred to as a computing device. At block 500, a computing device obtains a first position of a tracking unit, which has an inertial measurement unit and a visual marker configured to be tracked by a camera. At block 502, the computing device computes a first distance between the automated fixture and the first position. At block 504, the computing device uses the first distance to compute a first control value for setting a function of the automated fixture to a first setting. At block 506, the computing device obtains a second position of the tracking unit. At block 508, the computing device computes a second distance between the automated fixture and the second position. At block 508, the computing device uses the second distance to compute a second control value for setting the function of the automated fixture to a second setting.

Many different automated fixtures and their functions are applicable to the principles described herein. A lighting fixture having zoom and iris functions are used in the examples provided herein, but are not meant to be limiting. Other examples of automated fixtures include cameras (e.g. functions are zoom, iris, focus, etc.), audio speakers (e.g. functions are volume of sound, treble level, bass level, etc.), gas or smoke machines (e.g. functions are rate of output of gas or smoke, type of smoke, etc.), water cannons (e.g. functions are water pressure output, water flow output, angle of water stream output, etc.) or fluid cannons in general, guns (e.g. functions are rate of fire, type of ammunition, etc.), and microphones (e.g. functions are sensitivity of microphone). Other automated fixtures also include multimedia projectors, which can vary the content being displayed or projected based on the position of the tracking unit. Multimedia projectors, such as LCD projectors for example, can also vary the focus, zoom, and other functions based on the position of the tracking unit. It can be appreciated that there may be other automated fixtures having functions which can be controlled using the principles described herein.

Turning to FIG. 22, another example embodiment of computer executable instructions is provided, which includes instructions specific to automated fixtures that have movement functionality. For example, robotic light fixtures, robotic camera fixtures, robotic water cannons, robotic microphones, etc., may use such an embodiment. As many of the operations are similar to those in FIG. 21, these operations are not explained in detail. In FIG. 22, after block 500, the computing device computes a control value for point the automated fixture at the first position (block 512). Blocks 502, 504 and 506 are implemented, Then, at block 514, the computing device computes a control value to point the automated fixture at the second position. Blocks 508 and 510 are also implemented after obtaining the second position.

Figure 23:
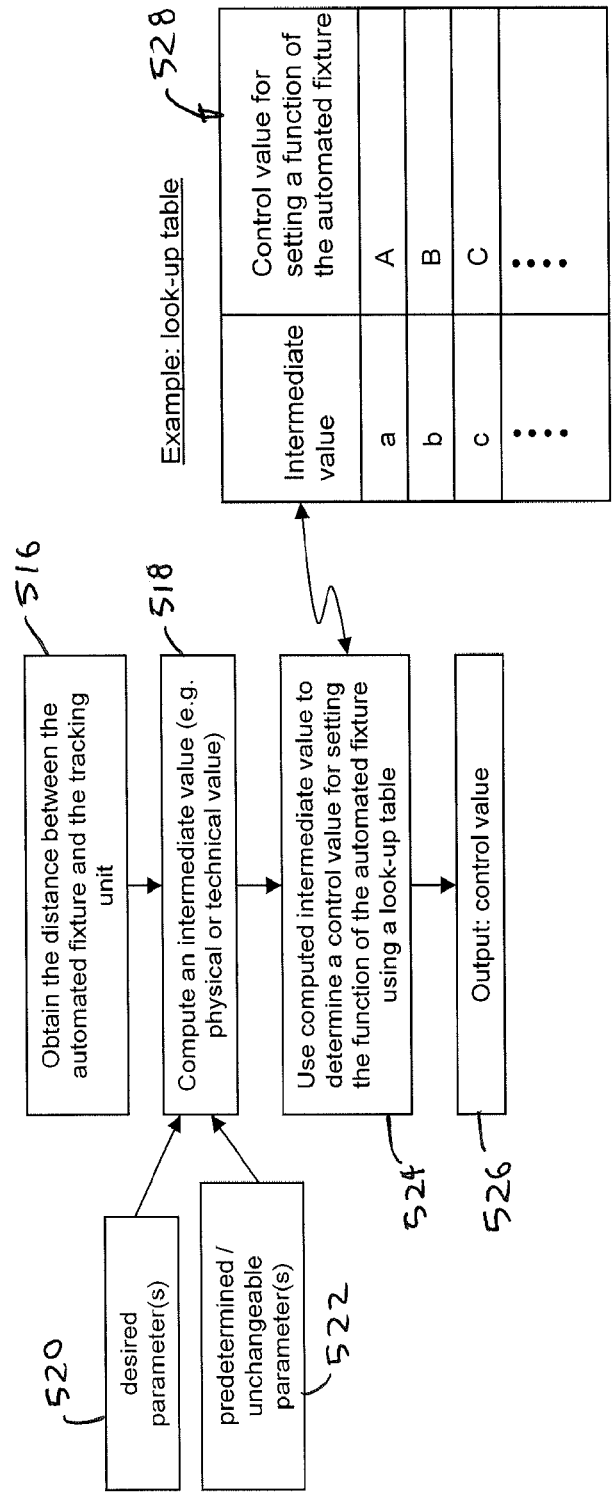
FIG. 23 is a flow diagram illustrating example computer executable instructions for computing a control value for setting the function of an automated fixture to a certain setting.

Turning to FIG. 23, an example embodiment of computer executable instructions is provided for computing a control value for setting the function of an automated fixture to a certain setting. For example, this embodiment can be used when implementing blocks 504 or 510, or both. In FIG. 23, the computing device obtains the distance between the automated fixture and the tracking unit (block 516). The computing device then computed an intermediate value using the distance (block 518). The intermediate value may be a physical value or a technical value which relates to the operation of the automated fixture. The computation at block 518 may also include desired parameters 520, and may also include predetermined or unchangeable parameters 522. After block 518, the computing device uses the computed intermediate value to determine the control value for setting the function of the automated fixture using a look-up table (block 524). An example embodiment of a look-up table 528 is shown, and it shows the mappings between intermediate values and control values for setting a function of the automated fixture. The look-up table is specific to the control of the automated fixture. At block 526, the control value is outputted.

Figure 24:
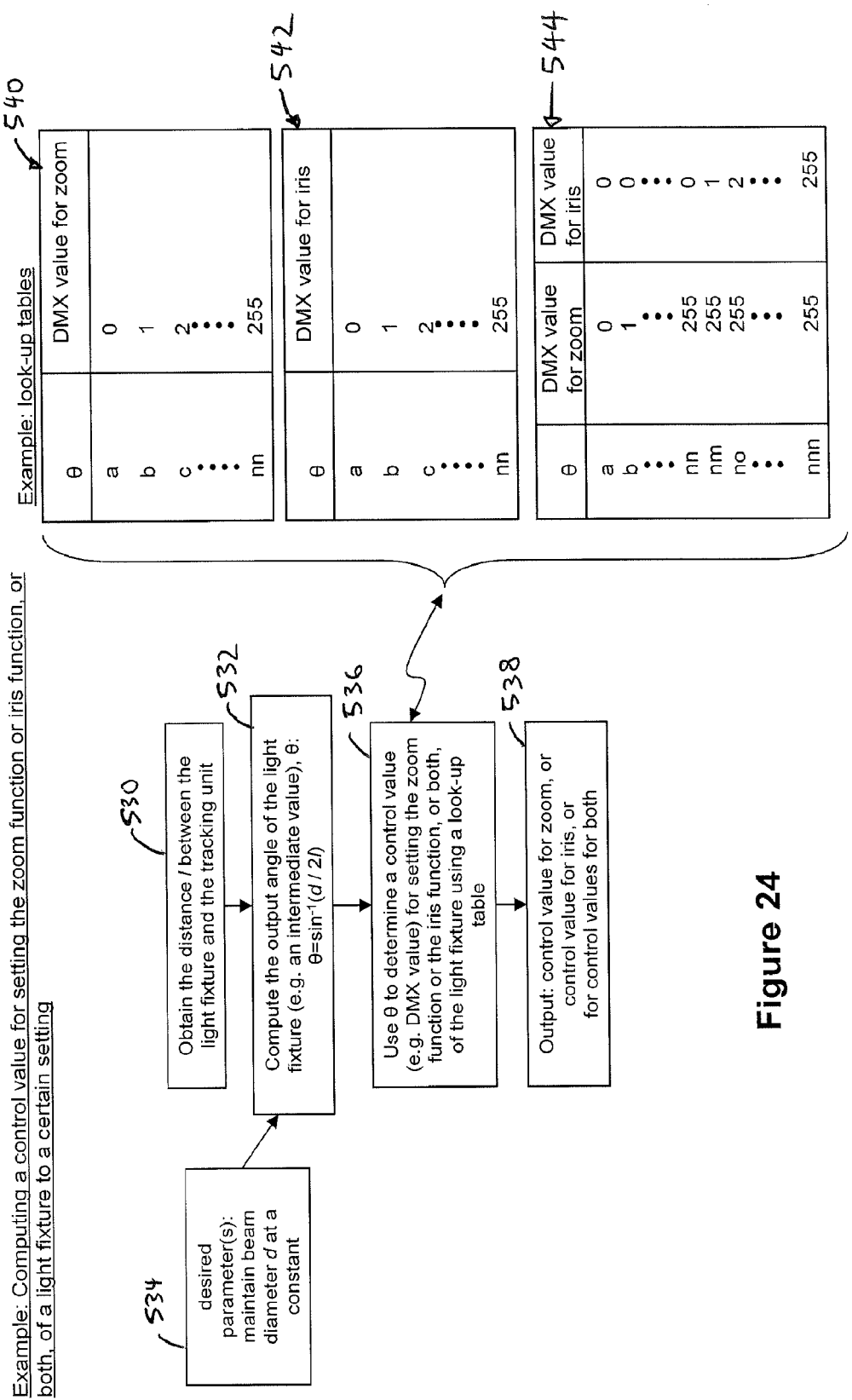
FIG. 24 is a flow diagram illustrating example computer executable instructions for computing a control value for setting the zoom function or iris function, or both, of a light fixture to a certain setting.

Turning to FIG. 24, an example embodiment that is similar to FIG. 23 is provided, but is specific to light fixtures, The computer executable instructions can, for example, be used with the instructions of FIG. 21 or 22 to maintain the beam diameter size being projected at the position of a tracking unit, even as the tracking unit changes position. This scenario is shown in FIGS. 20(a) and 20(b). In FIG. 24, the computer executable instructions are used to compute a control value for setting the zoom function or iris function, or both. The computing device obtains the distance l between the light fixture and the tracking unit (block 530). The computing device computes the output angle of the light fixture θ (e.g. the intermediate value). The output angle θ can be computed by $\theta = \sin^{-1}(d/2l)$. The value d is the desired beam diameter, which can be set to remain constant (block 534). At block 536, θ is used to determine a control value for setting the zoom function or the iris function, or both, of the light fixture using a look-up table. In an example embodiment, the control value is a DMX value used in a digital multiplex protocol for controlling lighting fixtures and other intelligent or automated fixtures.

The example look-up table 540 shows the mappings between θ values and DMX values for the zoom function. For example, this table 540 is used when controlling the beam diameter using only the zoom function. The DMX values range, for example, from 0 to 255. The example look-up table 542 shows the mappings between θ values and DMX values for the iris function. For example, this table 542 is used when controlling the beam diameter using only the iris function. The example look-up table 544 shows the mappings between θ values and both DMX values for the zoom function and the iris function. For example, this table can be used when controlling the beam diameter using a combination of the zoom and iris functions.

In the example shown in look-up table 544, the zoom function is used first to control the beam diameters for a number of values of θ. In other words, if the computed beam angle output of θ can be achieved using the zoom function only, then as per the configuration of the look-up table, only the zoom function is used, and the iris function is not used. For example, for θ values a, b, . . . , nn, the DMX values 0-255 for zoom are used, and the DMX value for the iris function is maintained at 0 (e.g. a fully open position). In this way, a light operator person may maintain control of the iris function and manually adjust the iris setting as they wish. For example, there may be certain situations, where the light operator person may wish to use the iris function to manually black-out the light of the light fixture.

However, the zoom function may be limited to provide θ value, and thus a resulting beam diameter, that is small enough to match the desired beam diameter. For example when the DMX value for zoom is set to its maximum of 255, the angle θ is still not sufficiently small. Therefore, the iris function may be additionally combined with the use of the zoom function to achieve smaller angles of θ. Therefore, for smaller angles of θ, continuing as nm, no, . . . , nnn, the DMX value for zoom is maintained at 255, and the DMX values for the iris function range from 1 to 255.

The look-up tables shown are just examples, and the relationships for controlling the light fixture can be varied.

Continuing with FIG. 24, after block 536, the computing device outputs the control value for zoom, or the control value for iris, or control values for both.

Figure 25:
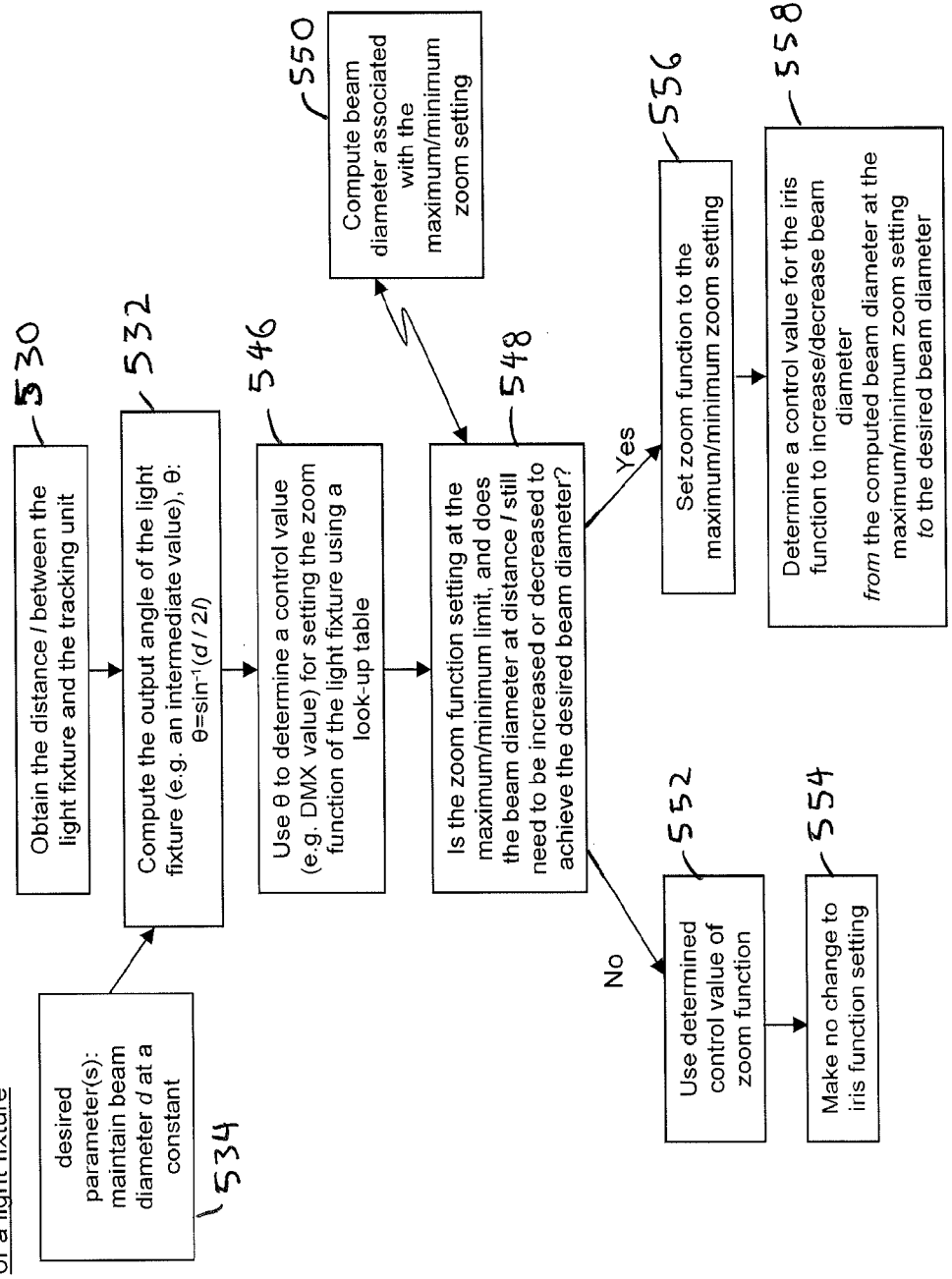
FIG. 25 is a flow diagram illustrating example computer executable instructions for computing a control value for setting the zoom function and the iris function of a light fixture to a certain setting.

Turning to FIG. 25, an example embodiment of computer executable instructions is provided for computing a control value for setting the zoom function and iris function. At block 530, the computing device obtains the distance l between the light fixture and the tracking unit. The computing device then computes the output angle of the light fixture θ (block 532). This computation 532 includes the desired parameter to maintain the beam diameter at a constant value. At block 546, the computing device uses θ to determine a control value for setting the zoom function of the light fixture using a look-up table for zoom settings. At block 548, the computing device determines if the zoom function setting is at the maximum or minimum limit, and if the beam diameter at distance l still needs to be increased or decreased to achieve the desired beam diameter. In an example embodiment, the computing device computes the beam diameter associated with the maximum or minimum zoom setting (block 550) to help determine if the beam diameter at distance l still needs to be increased or decreased to achieve the desired beam diameter.

If the condition of block 548 is not met, then the computing device outputs or uses the determined control value of the zoom function (block 552). No change is made to the iris function setting (block 554).

If the condition of block 548 is met, then the computing devices set the zoom function to the maximum or minimum zoom setting (block 556). The computing device also determines a control value for the iris function to increase or decrease the beam diameter, from the computed beam diameter at the maximum or minimum zoom setting, to the desired beam diameter.

The above example embodiment reduces the usage of the iris function, and activates the iris function in situations where the zoom function is not able to achieve the desired beam diameter settings. This may be advantageous to a light operator person who wishes to maintain manual control of the iris as much as possible.

For example, using the process of FIG. 25, when tracking unit is located 15 m away from the light fixture, the desired constant beam diameter is 0.5 m. However, the zoom function on the light fixture can only produced a beam diameter as small as 1 m (e.g. the max or min zoom setting). Therefore, in addition to setting the zoom function to produce a beam diameter of 1 m projected at 15 m away, the iris function is also set to further reduce the beam diameter from 1 m to 0.5 m.

Figure 26A:
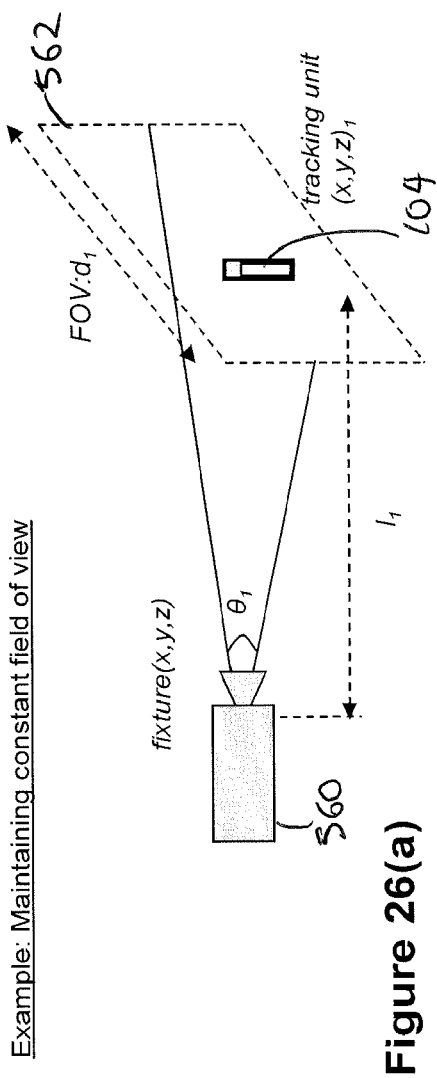
FIG. 26(a) is a schematic diagram of a camera fixture capturing a plane having a given field of view, with the plane including a first position of a tracking unit.

Turning to FIGS. 26(a) and (b), it can be appreciated that the principles and examples described with respect to light fixtures can be similarly applied to automated camera fixtures. For example, the principles for controlling zoom and iris to achieve a certain beam diameter in a light fixture application are similar to the principles for controlling zoom and iris to achieve a certain field of view in a camera application.

FIG. 26(a) shows a camera fixture 560 which has an angular field of view of $\theta_1$, Also shown is a plane 562, which includes the position of the tracking unit 104, and is located at a distance $l_1$ away from the camera fixture 560. The linear span of the field of view on the plane 562 is a distance of $d_1$.

Figure 26B:
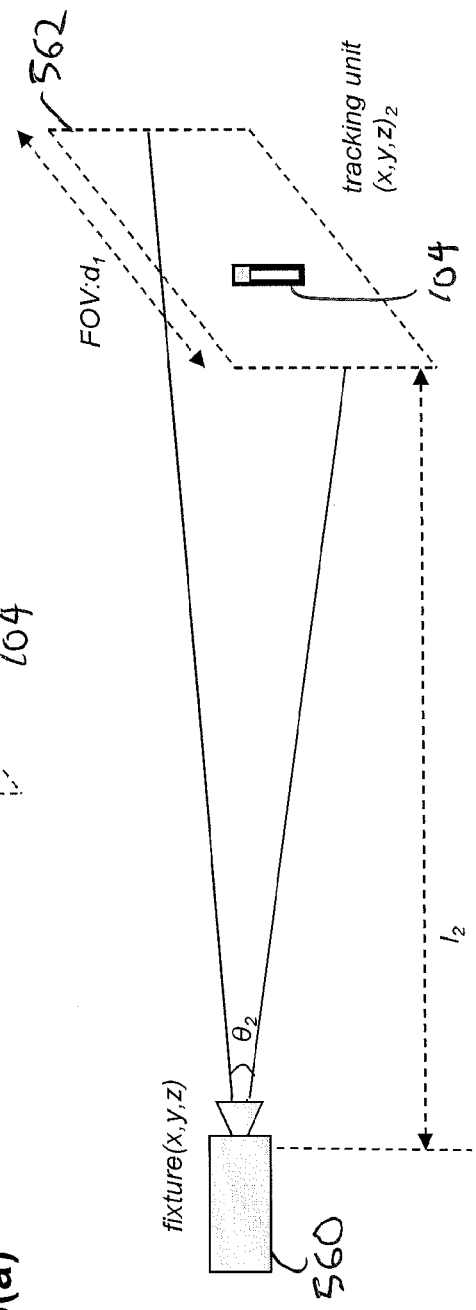

FIG. 26(b) shows that the tracking unit 104 has moved further away from the fixture 560 to a distance of $l_2$. To maintain the linear span distance of $d_1$ for the field of view projected on the plane 562, now located at a distance of $l_2$ away from the camera fixture, the angular field of view is adjusted to a different setting of $\theta_2$. The zoom function or iris function, or both, can be used to therefore maintain a constant linear span of the field of view projected on planes located at different distances, as marked by the position of the tracking unit.

Figure 27:
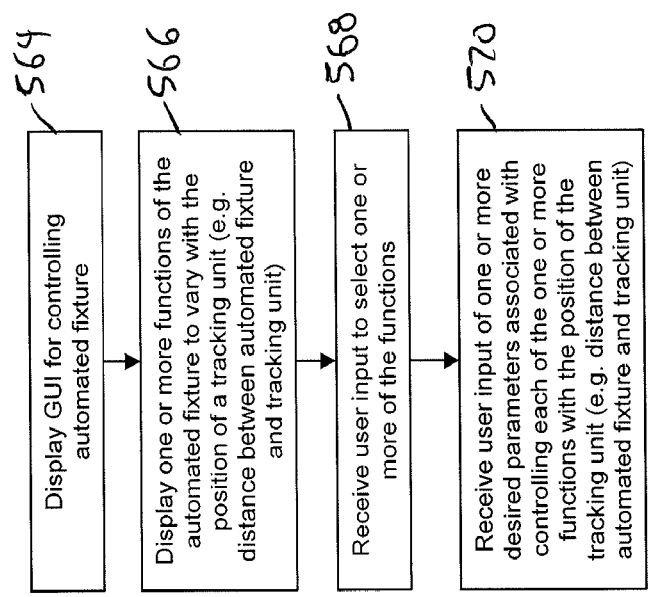
FIG. 27 is a flow diagram illustrating example computer executable instructions for displaying a graphical user interface (GUI) for selecting one or more functions to automatically control based on the position of a tracking unit.

A graphical user interface (GUI) can also be used to select the various functions of an automated fixture that are to be varied based on the position of a tracking unit. Turning to FIG. 27, an example embodiment of computer executable instructions is provided for a GUI to select functions of an automated fixture. At block 564, a computing device displays a GUI for controlling an automated fixture. At block 566, the computing device displays one or more functions of the automated fixture to vary with the position of a tracking unit (e.g. distance between automated fixture and tracking unit). At block 568, the computing device receives user input to select one or more of the functions. At block 570, the computing device receives user input of one or more desired parameters associated with controlling each of the one or more functions with the position of the tracking unit. The desired parameters may be a relationship or setting between the position of the tracking unit and the control of the automated fixture.

For example, the relationship may be set so that a function varies proportionally to the distance of the distance between the automated fixture and the tracking unit. In particular, the function of the automated fixture may vary in a linear proportional manner, or in an exponentially proportional manner. It can be appreciated that different relationships and parameters may be established to control the function of an automated fixture based on the position of a tracking unit.

Figures 28A, 28B:
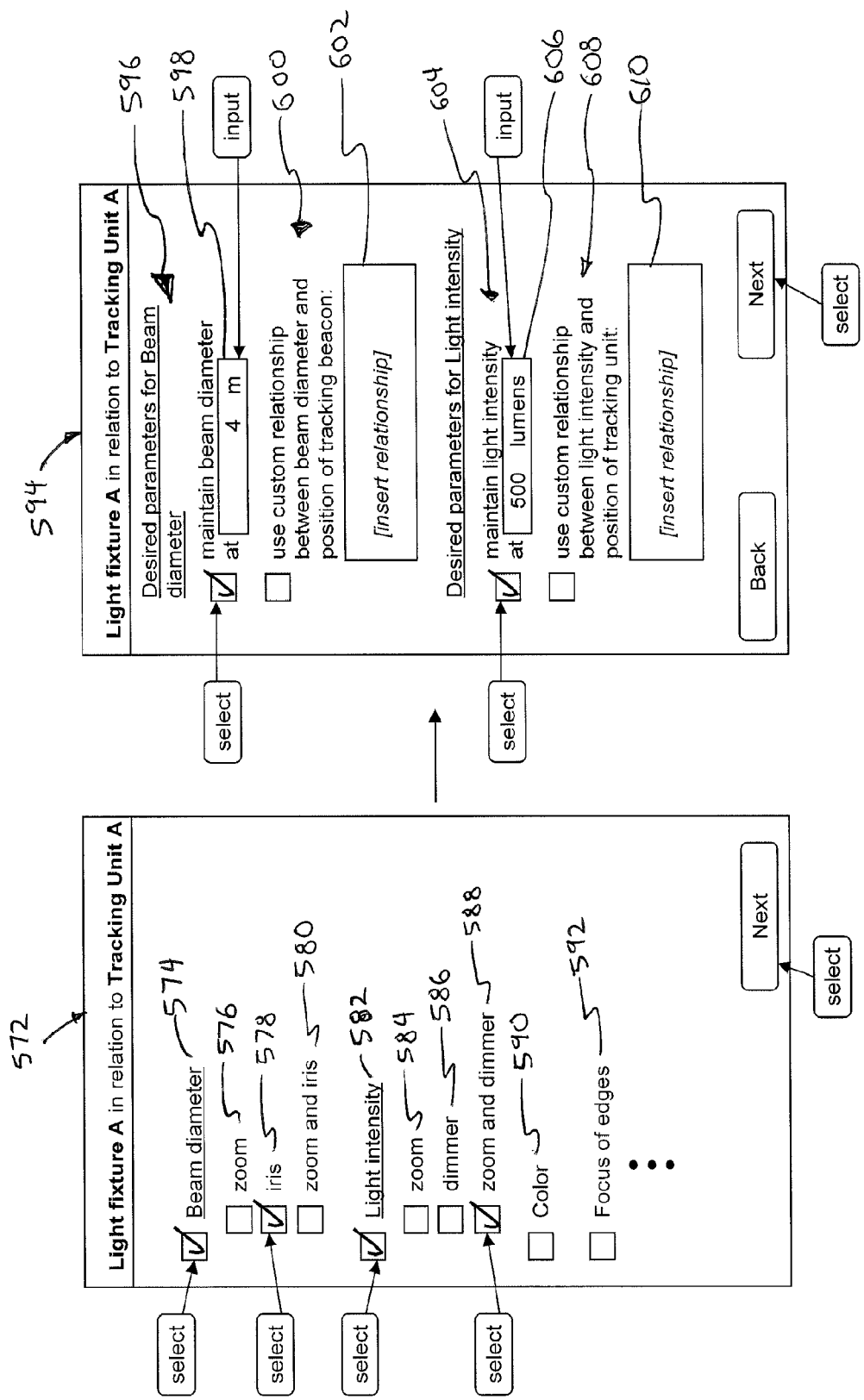
FIG. 28(a) is an example GUI for selecting functions to automatically control based on the position of a tracking unit.
FIG. 28(b) is an example GUI for inputting desired parameters associated with the automatic control.

Turning to FIGS. 28(a) and 28(b), an example embodiment of a GUI is shown. In FIG. 28(a), the GUI 572 shows functions of a light fixture that can be selected to change based on the position of a tracking unit. An option 574 is displayed to control the beam diameter. The beam diameter can be controlled using the zoom function (option 576), the iris function (option 578), or the zoom and the iris functions (option 580). An option 582 is displayed to control the light intensity, which can be controlled using the zoom function (option 584), the dimmer function (option 586), or the zoom and the dimmer function (option 588). For example, the light intensity can be controlled to maintain a light intensity at constant level. An option 590 is also displayed to control the color of the light. An option 592 is also displayed to control the focus of the edges. In the example shown, the user has selected to automatically control the beam diameter using the iris function and to automatically control the light intensity using the zoom and dimmer functions.

In a subsequent GUI 594, in FIG. 28(b), interfaces are provided for a user to input a relationship between the selected functions and the position of the tracking beacon. For the desired parameters of the beam diameter, an option 596 is displayed for maintain a constant sized beam diameter a given value. The option 596 includes an input field 598 to enter in the given value for the constant beam diameter size. For example, the user has selected option 596 and has inputted a given value of 4 m in the input field 598. In other words, the beam diameter will be maintained at a constant value of 4 m by automatically setting the iris function.

The user may alternatively enter in a custom relationship between the beam diameter and the position of the tracking unit using option 600, which includes an input field 602 to define the custom relationship.

An example of a custom relationship is to exponentially vary the size of the beam diameter between a tracking unit's first position and a tracking unit's second position.

Another example of a custom relationship is to maintain a constant beam diameter of Xm when the tracking unit is positioned in a certain area, and to maintain a constant beam diameter of Ym when the tracking unit is positioned in a different certain area.

Continuing with the GUI 594, the desired parameters for the light intensity can also be entered. An option 604 is displayed to maintain a light intensity at a given value. The option 604 includes an input field 606 to enter in the given value for the constant light intensity. For example, the user has selected option 604 and has inputted a given value of 500 lumens in the input field 606. In other words, the light intensity will be maintained at a constant value of 500 lumens by automatically setting the zoom and dimmer functions.

In another example embodiment, the desired parameter for the light intensity is not entered in by a user, but is set using a light meter. For example, a reading or measurement provided by a light meter is obtained and is used to automatically set the desired light intensity value to be maintained at different distances.

In an example method of setting the control of the light intensity, a light meter is used to obtain a first light intensity reading at a first distance, and the first setting or settings of the zoom or dimmer functions associated with the first light intensity reading are recorded. At a second, i.e. different, distance, and the zoom or dimmer functions, or both, are set to a second setting to provide the same first light intensity reading measured using the light meter at the second distance. The control value for the zoom or the dimmer functions, or both, will be set to vary in a linear manner between the first setting and the second setting, as a tracking unit moves between the first distance and the second distance.

The user may alternatively enter in a custom relationship between the light intensity and the position of the tracking unit using option 608, which includes an input field 310 to define the custom relationship.

Figure 29A:
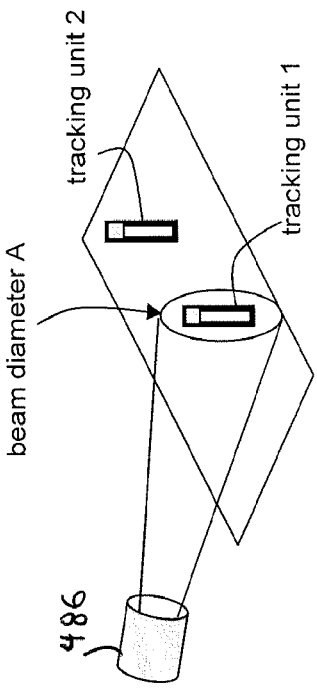
FIG. 29(a) is a schematic diagram of a light fixture shining a beam of a first diameter on a first tracking unit.
Figure 29B:
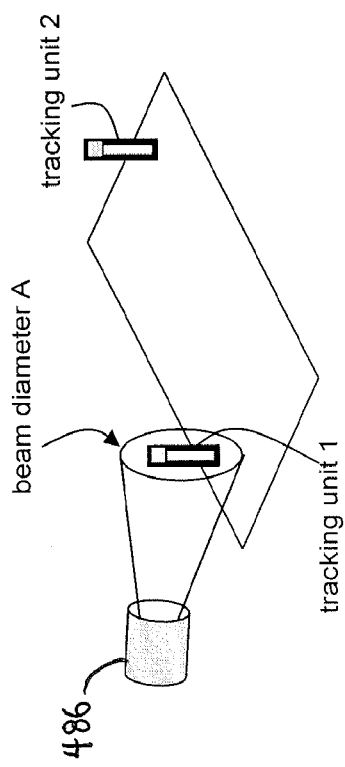
FIG. 29(b) shows the light fixture shining a beam of the same first diameter on the first tracking unit as the tracking unit changes position.
Figure 29C:
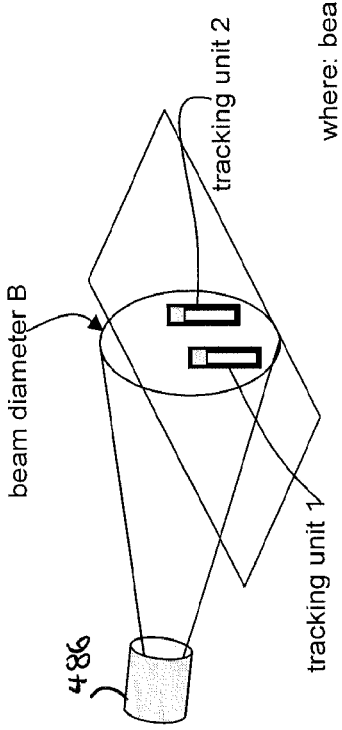
FIG. 29(c) shows the light fixture shining a beam of a second diameter on the first tracking unit and a second tracking unit that is located within a predetermined distance of the first tracking unit.

Turning to FIGS. 29(*a*), 29(*b*) and 29(*c*), an example scenario is displayed in which the size of a beam diameter is automatically increased to accommodate two or more tracking units. In FIG. 29(*a*), the light fixture 486 is tracking a first tracking unit and maintains a constant beam diameter size (e.g. beam diameter A) at the position of the first tracking unit. A second tracking unit is also located in the general area. However, the light fixture does not illuminate the position of the tracking unit since it is located too far from the first tracking unit.

In FIG. 29(*b*), even as the first and the second tracking units move around, the light fixture will maintain a constant beam diameter size (e.g. beam diameter A) on the first tracking unit only if the second tracking unit is positioned more than a predetermined distance from the first tracking unit.

In FIG. 29(*c*), when the second tracking unit is detected to be within a predetermined distance from the first tracking unit, the light fixture 486 will produce an increased beam diameter size (e.g. beam diameter B) that will illuminate both the first and the second tracking units.

Figure 30:
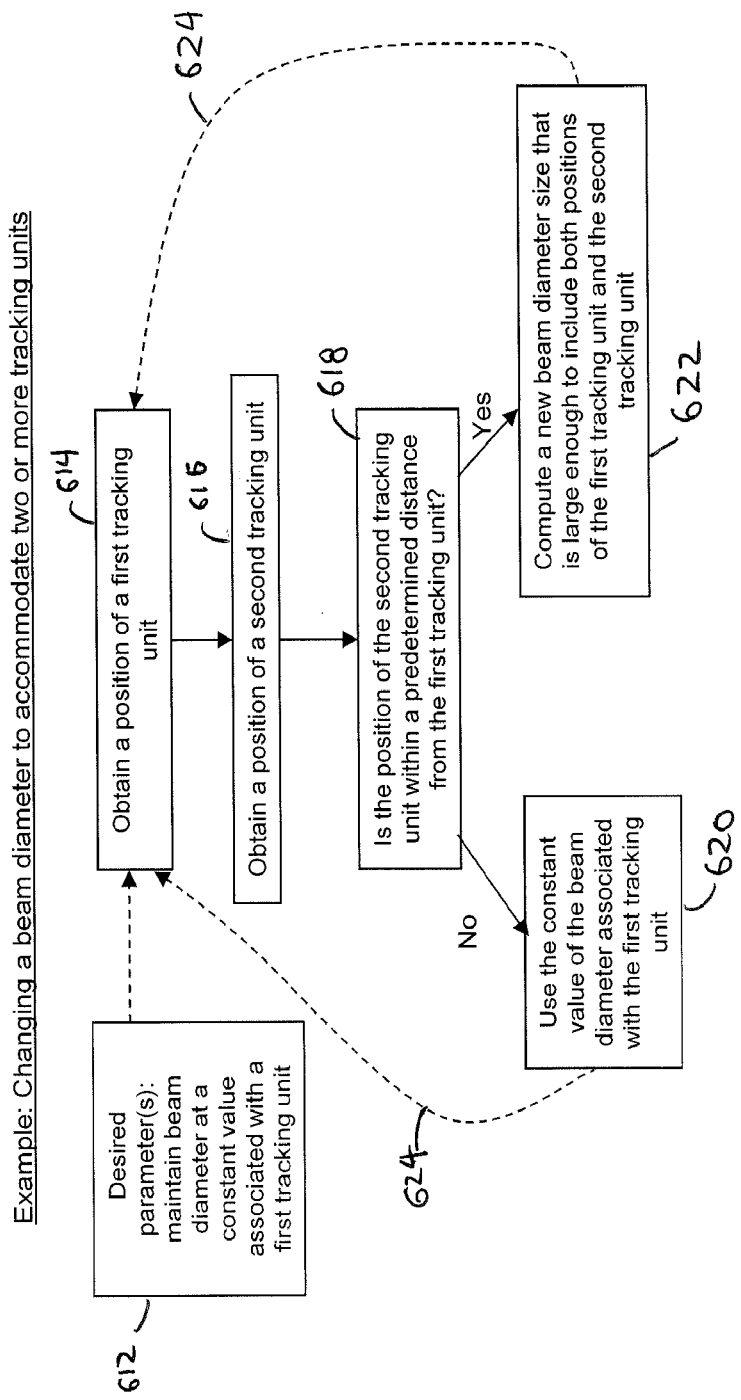
FIG. 30 is a flow diagram illustrating example computer executable instructions for changing a beam diameter to accommodate two or more tracking units.

Turning to FIG. 30, an example embodiment of computer executable instructions is provided for changing a beam diameter to accommodate two or more tracking units. These instructions can be also used to vary the field of view of a camera to accommodate two or more tracking units.

The process may include obtaining a parameter that defines maintaining a beam diameter at a constant value associated with a first tracking unit (block 612). At block 614, a computing device obtains a position of a first tracking unit. At block 616, the computing device obtains a position of the second tracking unit. At block 618, the computing device determines if the position of the second tracking unit is within a predetermined distance from the first tracking unit. If not, at block 620, the computing device uses the constant value of the beam diameter associated with the first tracking unit. If the position of the second tracking unit is within a predetermined distance from the first tracking unit, the computing device computes a new beam diameter size that is large enough to include both positions of the first and the second tracking units (block 622). As shown by dotted lines 624, the process can be repeated so as to illuminate the first tracking unit, or the combination of the first and second tracking units as the tracking units change positions.

Although not shown, in another example aspect, continuing after block 620, the computing device computes a control signal to point the beam at the first tracking unit. In other words, if the second tracking unit is not close enough, the light fixture continues to follow the position of the first tracking unit.

Although not shown, in another example aspect, continuing after block 622, the computing device computes a new target position between the first and the second tracking units, and the light fixture is pointed at the new target position. In an example aspect, the new target position bisects a line defined between the positions of the first tracking unit and the second tracking unit.

Although a second tracking unit is described in the above examples, multiple other tracking units can be used according to similar principles. For example, if multiple other tracking units are within a predetermined distance to the first tracking unit, a new beam diameter is computed to encompass all positions of the first tracking unit and the other multiple tracking units. Additionally, for example, a perimeter is computed that encompasses all the positions of the first tracking unit and the other multiple tracking units, and a new target position located within the perimeter is computed. The light fixture then points the beam, having the new beam diameter, at the new target position.

In a general example, a method is provide for controlling a function of an automated fixture configured to interact with an area in physical space. The method includes: obtaining a default size of the area; obtaining the position of the first tracking unit and a position of a second tracking unit; determining if the position of the second tracking unit is within a predetermined distance from the second tracking unit; if so, computing a new size of the area that includes the position of the first tracking unit and the second tracking unit; and if not, using the default size of the area that includes the position of the first tracking unit.

In another aspect, the automated fixture is a light fixture configured to project a beam of light in the physical space. In another aspect, the automated fixture is a camera fixture configured to record images with a field of view in the physical space.

It can be appreciated that the principles of changing the setting of a function of an automated fixture can be based on the change of relative distance between the automated fixture and the tracking unit. For example, the automated fixture can move and change positions, thereby changing the distance relative to the tracking unit. In another example, both the tracking unit and automated fixture may move, and the change in the relative distance may be used to vary a setting of a function in the automated fixture.

Figure 31A:
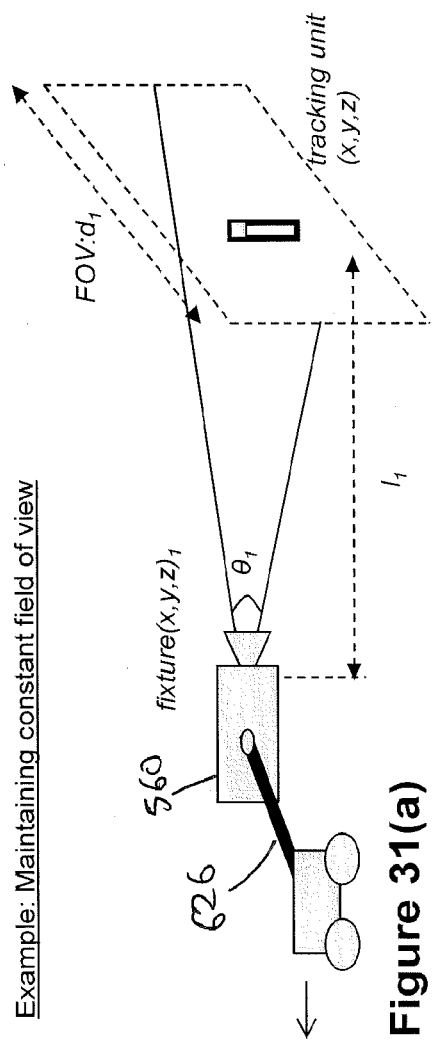
FIG. 31(a) is a schematic diagram of a camera fixture capturing a plane having a given field of view, with the plane including a first position of a tracking unit.
Figure 31B:
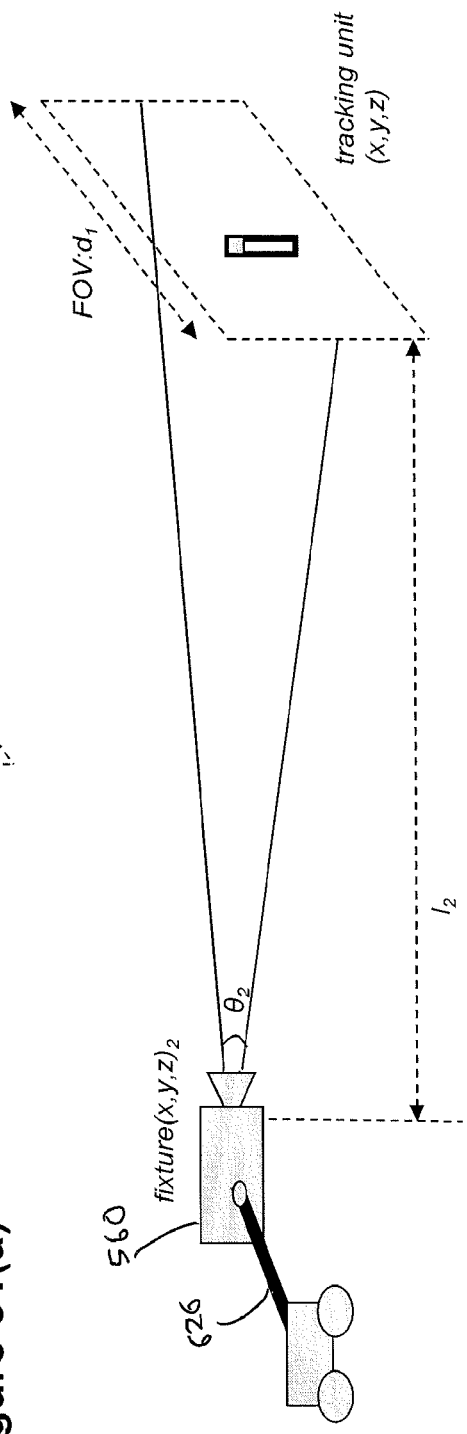
FIG. 31(b) shows the camera fixture in a different position relative to the tracking unit and capturing a plane with the same given field of view, with the plane including a second position of the tracking unit.

For example, turning to FIG. 31(*a*), a camera fixture 560 mounted on a moving light boom 626 is able to move the camera away from the position of the tracking unit. As shown in FIG. 31(*b*), when the distance between the camera and the tracking unit changes from $l_1$ to $l_2$, the linear span of the field of view of the plane marked by the tracking unit's position remains the same at a value of $d_1$.

In another example embodiment, although the above examples describe varying a setting of a function based on the relative distance between the automated fixture and the tracking unit 104, it can be appreciated that similar principles apply to describe varying a setting of a function based on the relative orientation angle between the automated fixture and the tracking unit 104. Similar principles apply to describe varying a setting of a function based on the relative velocity or the relative acceleration between the automated fixture and the tracking unit 104. For example, as the angular orientation of the tracking unit changes relative to a lighting fixture, the light intensity may increase or decrease, or the beam diameter may increase or decrease. In another example, as the angular orientation of the tracking unit changes relative to a camera fixture, the focus setting may increase or decrease.

The examples provided herein may be applied to various automated fixtures and their applicable functions.

The schematics and block diagrams used herein are just for example. Different configurations and names of components can be used. For instance, components and modules can be added, deleted, modified, or arranged with differing connections without departing from the spirit of the invention or inventions.

The steps or operations in the flow charts and diagrams described herein are just for example. There may be many variations to these steps or operations without departing from the spirit of the invention or inventions. For instance, the steps may be performed in a differing order, or steps may be added, deleted, or modified.

It will be appreciated that the particular embodiments shown in the figures and described above are for illustrative purposes only and many other variations can be used according to the principles described. Although the above has been described with reference to certain specific embodiments, various modifications thereof will be apparent to those skilled in the art as outlined in the appended claims.

The invention claimed is:

1. A method for controlling a function of an automated fixture comprising:
   obtaining a first position of a tracking unit, the tracking unit comprising a light source and the obtaining the first position comprising:
      obtaining a first set of images of the light source, the images captured by at least two or more cameras;
      determining a position of the light source by determining a pixel location of the light source in the first set of images and applying triangulation to the first set of images;
      establishing the position of the light source as the first position of the tracking unit;
   computing a first distance between the automated fixture and the first position of the tracking unit, the computing the first distance comprising computing a difference between coordinates of the automated fixture and coordinates of the first position of the tracking unit;
   using the first distance to set a function of the automated fixture to a first setting, wherein interaction of the automated fixture at the first position of the tracking unit is characterized by a parameter value;
   obtaining a second position of the tracking unit, the obtaining the second position comprising:
      obtaining a second set of images of the light source;
      determining a second position of the light source by determining another pixel location of the light source in the second set of images and applying triangulation to the second set of images;
      establishing the second position of the light source as the second position of the tracking unit;
   computing a second distance between the automated fixture and the second position of the tracking unit, the computing the second distance comprising computing a difference between the coordinates of the automated fixture and coordinates of the second position of the tracking unit; and
   using the second distance and the parameter value to set the function of the automated fixture to a second setting and wherein interaction of the automated fixture at the second position of the tracking unit is also characterized by the parameter value.

2. The method of claim 1 further comprising, after obtaining the first position, computing a control value to point the automated fixture at the first position; and, after obtaining the second position, computing a control value to point the automated fixture at the second position.

3. The method of claim 2 wherein the automated fixture is a fixture that projects light.

4. The method of claim 3 wherein the function is a zoom function; the parameter value is a given light beam diameter; and the first setting of the zoom function is set to provide the given light beam diameter projected at the first position, and the second setting of the zoom function is set to provide the same light beam diameter projected at the second position.

5. The method of claim 3 wherein the function is a zoom function; the parameter value is a given light intensity; and the first setting of the zoom function is set to provide the given light intensity projected at the first position, and the second setting of the zoom function is set to provide the same light intensity projected at the second position.

6. The method of claim 3 wherein the automated fixture is a multimedia projector.

7. The method of claim 3 wherein the function is an iris function; the parameter value is a given light beam diameter; and the first setting of the iris function is set to provide the given light beam diameter projected at the first position, and the second setting of the iris function is set to provide the same light beam diameter projected at the second position.

8. The method of claim 2 wherein the automated fixture projects light and the function comprises a zoom function and an iris function.

9. The method of claim 8 wherein the zoom function and the iris function are set to maintain a constant beam diameter projected at the first position and the second position.

10. The method of claim 9 wherein the iris function setting is changed when the zoom function is set to a maximum or minimum value, and a beam diameter associated with the maximum or minimum value of the zoom function needs to be further increased or decreased to provide the constant beam diameter.

11. The method of claim 2 wherein the automated fixture is a camera fixture.

12. The method of claim 11 wherein the function is a zoom function.

13. The method of claim 12 wherein the parameter value is a given field of view and the first setting of the zoom function is set to provide the given field of view at a first plane that includes the first position, and the second setting of the zoom function is set to provide the same field of view at a second plane that includes the second position.

14. The method of claim 11 wherein the function is a focus function.

15. The method of claim 14 wherein the parameter value is a focus value and the first setting of the focus function is set to provide the focus level at a first plane that includes the first position, and the second setting of the focus function is set to provide the same focus level at a second plane that includes the second position.

16. The method of claim 1 wherein the difference between the first setting and the second setting is proportional to the difference between the first distance and the second distance.

17. The method of claim 16 wherein the difference between the first setting and the second setting is linearly proportional to the difference between the first distance and the second distance.

18. The method of claim 1 wherein the automated fixture is an audio fixture.

19. A computing system comprising a processor, a communication device and a non-transitory computer readable medium, the non-transitory computer readable medium comprising executable instructions for controlling a function of an automated fixture, the executable instructions comprising:
   obtaining a first position of a tracking unit, the tracking unit comprising a light source and the obtaining the first position comprising:
      obtaining a first set of images of the light source, the images captured by at least two or more cameras;
      determining a position of the light source by determining a pixel location of the light source in the first set of images and applying triangulation to the first set of images;

establishing the position of the light source as the first position of the tracking unit;

computing a first distance between the automated fixture and the first position of the tracking unit, the computing the first distance comprising computing a difference between coordinates of the automated fixture and coordinates of the first position of the tracking unit;

using the first distance to set a function of the automated fixture to a first setting, wherein interaction of the automated fixture at the first position of the tracking unit is characterized by a parameter value;

obtaining a second position of the tracking unit, the obtaining the second position comprising:
  obtaining a second set of images of the light source;
  determining a second position of the light source by determining another pixel location of the light source in the second set of images and applying triangulation to the second set of images;
  establishing the second position of the light source as the second position of the tracking unit;

computing a second distance between the automated fixture and the second position of the tracking unit, the computing the second distance comprising computing a difference between the coordinates of the automated fixture and coordinates of the second position of the tracking unit; and using the second distance and the parameter value to set the function of the automated fixture to a second setting and wherein interaction of the automated fixture at the second position of the tracking unit is also characterized by the parameter value.

20. The computing system of claim 19 wherein the executable instructions further comprise: after obtaining the first position, computing a control value to point the automated fixture at the first position; and, after obtaining the second position, computing a control value to point the automated fixture at the second position.

21. The computing system of claim 20 wherein the automated fixture is a fixture that projects light.

22. The computing system of claim 21 wherein the function is a zoom function; the parameter value is a given light beam diameter; and the first setting of the zoom function is set to provide the given light beam diameter projected at the first position, and the second setting of the zoom function is set to provide the same light beam diameter projected at the second position.

23. The computing system of claim 21 wherein the function is a zoom function; the parameter value is a given light intensity; and the first setting of the zoom function is set to provide the given light intensity projected at the first position, and the second setting of the zoom function is set to provide the same light intensity projected at the second position.

24. The computing system of claim 19 wherein the automated fixture is a multimedia projector that projects light.

25. The computing system of claim 21 wherein the function is an iris function; the parameter value is a given light beam diameter; and the first setting of the iris function is set to provide the given light beam diameter projected at the first position, and the second setting of the iris function is set to provide the same light beam diameter projected at the second position.

26. The computing system of claim 20 wherein the automated fixture projects light and the function comprises a zoom function and an iris function.

27. The computing system of claim 26 wherein the zoom function and the iris function are set to maintain a constant beam diameter projected at the first position and the second position.

28. The computing system of claim 27 wherein the iris function setting is changed when the zoom function is set to a maximum or minimum value, and a beam diameter associated with the maximum or minimum value of the zoom function needs to be further increased or decreased to provide the constant beam diameter.

29. The computing system of claim 19 wherein the automated fixture is a camera fixture.

30. The computing system of claim 29 wherein the function is a zoom function.

31. The computing system of claim 30 wherein the parameter value is a given field of view and the first setting of the zoom function is set to provide the given field of view at a first plane that includes the first position, and the second setting of the zoom function is set to provide the same field of view at a second plane that includes the second position.

32. The computing system of claim 29 wherein the function is a focus function.

33. The computing system of claim 32 wherein the parameter value is a focus value and the first setting of the focus function is set to provide the focus level at a first plane that includes the first position, and the second setting of the focus function is set to provide the same focus level at a second plane that includes the second position.

34. The computing system of claim 19 wherein the difference between the first setting and the second setting is proportional to the difference between the first distance and the second distance.

35. The computing system of claim 34 wherein the difference between the first setting and the second setting is linearly proportional to the difference between the first distance and the second distance.

36. The computing system of claim 19 wherein the automated fixture is an audio fixture.

37. A non-transitory computer readable medium comprising executable instructions for controlling a function of an automated fixture, the executable instructions configured to be executed by a processor, the executable instructions comprising:

obtaining a first position of a tracking unit, the tracking unit comprising a light source and the obtaining the first position comprising:
  obtaining a first set of images of the light source, the images captured by at least two or more cameras;
  determining a position of the light source by determining a pixel location of the light source in the first set of images and applying triangulation to the first set of images;
  establishing the position of the light source as the first position of the tracking unit;

computing a first distance between the automated fixture and the first position of the tracking unit, the computing the first distance comprising computing a difference between coordinates of the automated fixture and coordinates of the first position of the tracking unit;

using the first distance to set a function of the automated fixture to a first setting, wherein interaction of the automated fixture at the first position of the tracking unit is characterized by a parameter value;

obtaining a second position of the tracking unit, the obtaining the second position comprising:
  obtaining a second set of images of the light source;

determining a second position of the light source by determining another pixel location of the light source in the second set of images and applying triangulation to the second set of images;

establishing the second position of the light source as the second position of the tracking unit;

computing a second distance between the automated fixture and the second position of the tracking unit, the computing the second distance comprising computing a difference between the coordinates of the automated fixture and coordinates of the second position of the tracking unit; and using the second distance and the parameter value to set the function of the automated fixture to a second setting and wherein interaction of the automated fixture at the second position of the tracking unit is also characterized by the parameter value.

\* \* \* \* \*